US006048900A

United States Patent [19]
Connell et al.

[11] Patent Number: 6,048,900
[45] Date of Patent: Apr. 11, 2000

[54] AMIDE DERIVATIVES AND METHODS FOR USING THE SAME AS SELECTIVE NEUROPEPTIDE Y RECEPTOR ANTAGONISTS

[75] Inventors: Richard D. Connell, Trumbull; Timothy G. Lease, Guilford; Gaetan H. Ladouceur, Branford, all of Conn.; Martin H. Osterhout, Raleigh, N.C.

[73] Assignee: Bayer Corporation, West Haven, Conn.

[21] Appl. No.: 09/023,498

[22] Filed: Feb. 13, 1998

[51] Int. Cl.[7] ..................................... A01N 33/08
[52] U.S. Cl. ..................... 514/663; 514/665; 514/670
[58] Field of Search .................... 514/663, 665, 514/670

[56] References Cited

U.S. PATENT DOCUMENTS

| | | | |
|---|---|---|---|
| 2,109,698 | 3/1938 | Harman | 18/53 |
| 2,186,769 | 1/1940 | Schrim | 260/377 |
| 4,123,530 | 10/1978 | Corvi-Mora | 424/250 |
| 5,506,258 | 4/1996 | Christophe et al. | 514/423 |
| 5,552,411 | 9/1996 | Downing et al. | 514/312 |
| 5,554,621 | 9/1996 | Poindexter et al. | 514/278 |
| 5,571,921 | 11/1996 | Bender et al. | 546/199 |
| 5,602,024 | 2/1997 | Gerald et al. | 435/325 |
| 5,635,503 | 6/1997 | Poindexter et al. | 514/218 |

FOREIGN PATENT DOCUMENTS

| | | |
|---|---|---|
| 2037433 | 10/1991 | Canada . |
| 0 448 765 | 10/1991 | European Pat. Off. . |
| 0 628 555 | 12/1994 | European Pat. Off. . |
| 747 357A2 | 6/1995 | European Pat. Off. . |
| 0 747 356 | 12/1996 | European Pat. Off. . |
| 544892 | 2/1932 | Germany . |
| 575858 | 4/1933 | Germany . |
| 942195 | 11/1963 | United Kingdom . |
| WO 92/06079 | 4/1992 | WIPO . |
| WO 96/12489 | 5/1996 | WIPO . |
| WO 96/12490 | 5/1996 | WIPO . |
| WO 96/14307 | 5/1996 | WIPO . |
| WO 96/40660 | 12/1996 | WIPO . |

OTHER PUBLICATIONS

Prager, B. et al. *Verlag Von Julius Springer*, 4th ed. vol. IX, p. 213, "Beilsteins Handbuch der Organischen Chemie" (1926) (Translation Enclosed).

Boit, *Springer–Verlag*, p. 251 "Beilsteins Handbuch der Oranische Chemie, Viertes Erganzungswerk, Vierter Band, Erster Teil" 2–Methoxy–N–methyl–acetamid, N–Methyl–2–methylmercapto–acetamid (1977) (Translation enclosed).

Hellstrom et al., *Chem. Ber.*, vol. 69, pp. 1999–2003 "Ueber Alkyl–thioglykolsaure–anilide bzw.–p–toluidide and entsprechende Thionyl–Verbindungen" (1936) (Translation enclosed).

Lambling, *Bull.Chem.Soc.Fr.*, vol. 17, pp. 356–362 "Action de l'isocyanate de phenyle sur quelques acides–ethers" (1897) (Translation enclosed).

Budavari, S. et al. *The Merck Index*, p. 10, "Merck Research Laboratories, 47. Acetanilide" (1996).

Ghosh et al. *Curr. Sci.*, vol. 42, No. 3, pp. 92–94 Synthesis and pharmacology of simple analogues of reserpine (tertiary aminoacetyl derivatives of aniline and m–methoxyaniline) (1973).

Vasvari–Debreczy et al., *Tetrahedron*, vol. 37, No. 24, pp. 4337–4342, "Oxidative cyclization of 2–pyrrolidinylacetamide and 2–pyrrolidinyl–propionamide local anaesthetics" (1981).

Larocca et al., *Journal of Pharmaceutical Sciences*, vol. 54, No. 4, pp. 654–655 "Synthesis of Some SubstitutedAminoactylbenzamides for Pharmacological Study" (1965).

El–Barbary et al., *Tetrahedron*, vol. 38, No. 3, pp. 405–412 "Enamine chemistry–XXIV. Synthesis, Thiation and Reduction of Lactams" (1982).

Oklobdzija et al., *Journal of Heterocyclic Chemistry*, vol. 20, No. 7, pp. 1335–1338\ "Synthesis of pyrazolo[4.3–d] oxazoles from 1–(2, 4–dinitrophenyl)–3–methyl–5–pyrazolon–4– oxime" (1983).

Maas et al., *Rec.Trav.Chim. Pays–Bas*, vol. 74, No. 2, pp. 175–180 "The action of diazoacetic ester on pyridone–2" (1955).

Reiter, *Tetrahedron Let.*, vol. 26, No. 29, pp. 3423–3426 "A general synthesis of 4(5)–acylimidazoles from 4–acylaminoisoxazoles" (1985).

Cornforth et al., *Tetrahedron Let.*, vol. 23, No. 21, pp. 2213–2216 "Failure to verify a reported synthesis of the aconitine skeleton" (1982).

Baker et al. *J. Med. Chem.*, vol. 10, No. 6, pp. 1129–1133 "Irreversible enzyme inhibitors. CVII. Proteolytic Enzymes. I. Bulk tolerance within chymotrypsin–inhibitor complexes" (1967).

Duffin et al., *J. Chem. Soc.*, pp. 734–739 Anhyro–compounds from nitrogen–containing derivatives of thioglycollic acid. Part I. Pyridine and Quinoline compounds (1951).

Misra, *J. Org. Chem*, vol. 23, pp. 897–899 "Certain thiazolo–benzimidazoles and thiazino–benzimidazoles" (1958).

(List continued on next page.)

*Primary Examiner*—Dwayne C. Jones
*Attorney, Agent, or Firm*—McDonell, Boehen Hulbert & Berghoff

[57] ABSTRACT

Amide derivatives and methods of administering the compositions to mammals to treat disorders such as obesity that are mediated by NPY and especially those mediated by NPY via the Y5 receptor.

13 Claims, No Drawings

OTHER PUBLICATIONS

Metz et al., *Tetrahedron*, vol. 50, No. 13, pp. 3951–3966 "Claisen rearrangement of N–Silyl Ketene N,O–Acetals Generated from Allyl N–Phenylimidates" (1994).

El–Sherief et al., *J. Indian Chem. Soc.*, vol. 60, No. 1 pp. 58–60 "Synthesis of Some New Benzoxazole, Benzthiazole and Benzimidazole Derivatives with Biological Activity" (1983).

Mahmoud et al., *J. Indian Chem. Soc.*, vol. 59, No. 5 "Synthesis and Biological Activity of Some New 2–(N–Substituted Carboxamidomethyl Thio)–Naphth[1–2,–d]Oxazoles–Part V" (1982).

U.S. Patent Application Serial No. 09/023,351 filed on Feb. 13, 1998 discloses a family of NPY5 Receptor Antagonists. The Patent Application and the above–referenced U.S. Patent Application are commonly owned.

Nair, *Indian Journal of Chemistry*, vol. 21B, pp. 4–7, Synthesis of $_{1,1}$–Diamino–2–acylethylenes–Sulphine Contraction Route (1982).

AMIDE DERIVATIVES AND METHODS FOR USING THE SAME AS SELECTIVE NEUROPEPTIDE Y RECEPTOR ANTAGONISTS

BACKGROUND OF THE INVENTION (1) Field of the Invention

This invention is a method for inhibiting the neuropeptide Y ("NPY") Y5 receptor using a class of amide derivatives. As antagonists of the Y5 receptor, the amide derivatives to are useful in treating obese mammals, mammals with bulimia, for treating mammals with obesity related disorders including, but not limited to type II diabetes, insulin resistance hyperlipidemia, hypertension, polycystic ovarian disease, pulmonary disease, sleep apnea, and for treating mammals suffering from NPY Y5 receptor inhibition related disorders such as memory disorders, epilepsy, dyslipidemia, and depression.

(2) Description of the Art

NPY is a 36 amino acid peptide that is a member of a larger peptide family which includes peptide YY (PYY), and pancreatic peptide (PP). NPY is highly conserved in a variety of animal, reptile and fish species and is found mainly in the central and peripheral sympathetic neurons. Furthermore, NPY is the most prevalent peptide in the mammalian brain where it is found primarily in the limbic regions. NPY has been found to elicit a number of physiological responses including appetite stimulation, anxiolysis, hypertension, and regulation of coronary tone.

NPY is believed to stimulate food intake by activating a hypothalamic eating receptor. Hu et al., J. Bio. Chem., Vol. 271, No. 42 pp.26315–319 (1996) discloses the isolation and identification and the expression cloning of a novel Y-type receptor from rat hypothalamus which the authors designated Y5. According to Hu et al., the localization of Y5 mRNA in critical areas of the brain hypothalamus and other brain regions known to regulate food intake together with an in vitro pharmacological profile consistent with the in vivo feeding data leads those skilled in the art to believe that the Y5 receptor is a primary mediator of NPY-induced feeding. A human homologue of the Y5 receptor has also been identified by Gerald et al., Nature, 382:168–171 (1996) which discloses the isolation, expression and analysis of an NPY Y5 receptor from the rat hypothalamus.

Antagonists of NPY receptors other than the Y5 receptors have been identified. For example, U.S. Pat. No. 5,554,621 discloses NPY antagonists that act on the Y1, Y2, Y3 and other Y1-like or Y4-type receptors. The reported antagonists are dihydropyridine based substituents.

U.S. Pat. No. 5,506,248 also discloses NPY receptor antagonists. The compositions disclosed each include sulphamadyl and amidino radicals. The disclosed compositions do not include amide moieties.

WO 96/16542 discloses genetically modified NPY receptors.

There is evidence that the Y5 receptor of NPY has a pharmacological feeding profile that is unique in comparison to other NPY receptors, namely, Y1, Y2, Y3 and Y4/PP1 because the Y5 receptor response correlates well with in vivo potencies of the standard peptides in the stimulation of feeding. Furthermore, antagonists of other NPY receptors such as Y1 do not necessarily exhibit an inhibitory response when assayed against Y5. In view of the knowledge that NPY plays an important role in eating and other disorders and in view of the knowledge that the Y5 receptor plays an important and unique role in the mechanism of such disorders, there is, therefore, a great need for antagonists of the NPY Y5 receptor. Furthermore, there is a need for antagonists of NPY that specifically target the Y5 receptor.

SUMMARY OF THE INVENTION

The present invention relates to methods for using amide derivatives that are NPY Y5 receptor antagonists to treat NPY mediated disorders including eating disorders such as bulimia and obesity. The present invention also includes novel amide derivatives. The 5 amide derivative described immediately below, except for compounds 330–362 disclosed in Table 4 are novel, while all of the compounds described below, including compounds 137–188 disclosed in Table 4 are useful in the methods disclosed herein.

One object of this invention is a novel class of amide derivatives having the formula

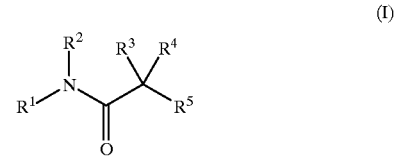

(I)

except that compounds of this invention do not include compounds 330–362 identified in Table 4.

Another object of this invention is a method for treating obesity, obesity related disorders and eating disorders in mammals using a therapeutically effective amount of a composition heretofore unknown for its NPY Y5 inhibitory properties.

It is another object of this invention to provide a method for the effective treatment of diseases that include the NPY Y5 receptor in their mechanism.

It is still another object of this invention to provide a method for the treatment of obesity and bulimia in humans using a new class of amide derivatives.

Another object of this invention are novel amide derivatives of the compound of formula (I) that are useful as NPY Y5 receptor antagonists and therapeutic compositions containing the same.

In one embodiment, this invention is a method for treating mammalian disorders mediated by the NPY Y5 receptor comprising the administration to a mammal of a therapeutically effective amount of at least one compound of formula (I) or pharmaceutically acceptable salts thereof wherein $R_1$–$R_5$ are each individually selected from the group of substituents including hydrogen, halogen, hydroxyl, thiol, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, and cyano.

In another embodiment, this invention is a method for treating mammalian disorders mediated by the NPY Y5 receptor comprising the administration to a mammal of a therapeutically effective amount of at least one compound having the general formula described above.

In yet another embodiment, this invention is a pharmaceutical dosage form comprising at least one amide derivative of a compound of formula (I) and at least one pharmaceutical additive.

DESCRIPTION OF THE CURRENT EMBODIMENT

The present invention relates to novel compositions that are NPY Y5 receptor antagonists and methods for using the compositions to treat NPY mediated disorders including eating disorders such as bulimia and obesity. Useful compositions of this invention are amide derivatives having the formula:

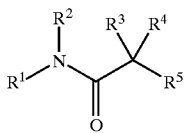

(I)

In the composition, $R^1$–$R^5$ are each individually selected from the group of substituents including hydrogen, halogen, hydroxyl, thiol, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, and cyano. $R^1$ is preferably selected from: cyclohexyl; benzoyl; phenyl; phenyl substituted at least once with a lower alkyl that is in turn substituted at least once with a substituent selected from cycloalkyl, alkoxy, furan, oxo, phenyl, diisopropylamine, alkoxy, or mixtures thereof, lower alkyl, alkyl substituted at least once by oxo, phenyl, or by mixtures thereof, phenyl substituted alkene, carboxamide, carboalkoxy, methyl substituted carbophenoxy, phenyldiazo, halogen, nitro, trifluoroalkyl, amino, phenyl substituted amino, lower alkyl substituted amino, aminoacyl, sulfonylphenyl, hydroxy, alkoxy, fluoro substituted phenyl, oxazole, phenoxy, thioalkoxy, and mixtures thereof; hydroxy or alkoxy substituted naphthyl; lH-indazole; fluorene; fluorene; and phenyl.

$R^2$ is preferably hydrogen, or a lower alkyl.

$R^3$ is preferably hydrogen or lower alkyl, phenyl, and most preferably hydrogen.

$R^4$ is preferably hydrogen or lower alkyl, phenyl, and most preferably hydrogen or methyl.

$R^5$ is preferably selected from substituents including: pyrrolidine; pyrrolidine substituted at least once by amino, acylamino, trifluoroacylamino, hydroxyl, carboxyl, carbobenzyloxyamino, carbomethoxyamino, carbotertbutoxyamino, alkyl substituted carbotertbutoxyamino, pyridine, lower alkyl, alkene, carboxamide, hydroxymethyl, aminoalkyl, pyrolidinemethyl, alkoxy methyl, carboxylmethyl, hydroxymethyl substituted at least once by phenyl and mixtures thereof; morpholine; piperazine substituted at least once with benzyl, phenyl, halogen substituted phenyl, and mixtures thereof; unsubstituted piperidine; substituted piperidine; piperidine substituted at least once by 2-oxo-2,3-dihydrobenzimidaz-1-ol, unsubstituted lower alkyl, lower alkyl substituted at least once by aminoethylamino, iodide, =O, piperidine, hydroxymethyl substituted piperidine, acylamino, hydroxyl, phenyl, and mixtures thereof, cyano, halogen, cyanomethylphenyl, piperidine, pyrrolidine, carboxyl, phenyl, phenyl substituted at least once by trifluoromethyl, lower alkyl, halogen, and mixtures thereof, 4-oxo-1-phenyl-1,3,8-triazaspiro[4.5dec-8-yl], hydroxyl, alkoxy, carboxyl amide having the formula $CONR^8R^9$ wherein $R^8$ and $R^9$ are each individually hydrogen or lower alkyl, or $R^8$ and $R^9$ are united with a nitrogen atom to form a piperidine substituent, amino alkyl having the formula $NR^{10}R^{11}$ where $R^{10}$ and $R^{11}$ are each individually selected from lower alkyl, cycloalkyl and phenyl, a ketone having the formula —$COR^{12}$ where $R^{12}$ is phenyl substituted by halogen or alkoxy or mixtures thereof, 3,6-dihydro-2H-pyridin-1-yl; halogen substituted phenyl substituted 3,6-dihydro-2H-pyridin-1-yl; 1,3,3-trimethyl-6-aza-bicyclo[3.2.1]octyl-6-yl; 2-aza-bicyclo[2.2.1]hept-6-yl; an amine having the formula $NR^6R^7$ where $R^6$ and $R^7$ are the each individually selected from hydrogen, unsubstituted and substituted alkyl having from 1 to 10 carbon atoms, cycloalkyl, alkene, carboxy substituted alkene, lower alkyl substituted at least once by cyano, alkyne, cycloalkyl, hydroxyl, 2-hydroxyethoxy, pyridine, piperidine, pyrrolidine, piperazine, morpholine, methylpiperazine, 1-Methylpyrrol, phenyl, phenyl substituted at least once by alkoxy, halogen, carboxyl, phenoxy, hydroxy, nitro, iodine, and mixtures thereof, imidazole, 5-nitropyridylamino, furan, benzo[1,3] dioxol-5-yl, indole, alkoxy substituted indole, diethylamino, alkoxy, carboxy, trifluoromethyl, lower alkyl, hydroxymethyl, and mixtures thereof, benzyl, phenyl, benzo[1,2,5]thiadiazol, pyridine, 1,2,4-triazole, and 3-oxo-cyclohex-1-en.

The following definitions apply to certain terms used herein.

The term "halogen" refers to fluorine, bromine, chlorine, and iodine atoms.

The term "hydroxyl" refers to the group —OH.

The term "furan" refers to a five membered oxygen containing saturated or unsaturated heterocycle.

The term "oxo" refers to the group =O.

The term "thiol" and "mercapto" refers to the groups —SH, and —$S(O)_{0-2}$, respectively.

The term "lower alkyl" refers to a cyclic, branched, or straight chain alkyl group of one to ten carbon atoms. This term is further exemplified by such groups as methyl, ethyl, n-propyl, i-propyl, n-butyl, t-butyl, i-butyl (or 2-methylpropyl), cyclopropylmethyl, i-amyl, n-amyl, hexyl and the like.

The term "substituted lower alkyl" refers to lower alkyl as just described including one or more substituents such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, heteroaryl, substituted heteroaryl, arylalkyl, heteroarylalkyl, alkyl alkenyl, alkyl alkynyl, alkyl cycloalkyl, alkyl cycloheteroalkyl, and cyano. These groups may be attached to any carbon atom of the lower alkyl moiety.

The term "alkenyl" refers to a group —R'C=CR"R'" where R', R", R'" are each individually selected from hydrogen, halogen, lower alkyl, substituted lower alkyl, acyl, aryl, substituted aryl, heteroaryl, substituted heteroaryl or the like.

The term "alkynyl" refers to a group —C≡C—R'; where R' is selected from hydrogen, halogen, lower alkyl, substituted lower alkyl, acyl, aryl, substituted aryl, heteroaryl, substituted heteroaryl or the like.

The term "alkyl alkenyl" refers to a group —R—CR'=CR'"R"", where R is lower alkyl, or substituted lower alkyl, R', R'", R"" are each independently selected from hydrogen, halogen, lower alkyl, substituted lower alkyl, acyl, aryl, substituted aryl, heteroaryl, or substituted heteroaryl.

The term "alkyl alkynyl" refers to a group —RC≡CR' where R is lower alkyl or substituted lower alkyl, R' is hydrogen, lower alkyl, substituted lower alkyl, acyl, aryl, substituted aryl, heteroaryl, or substituted heteroaryl.

The term "alkoxy" refers to the group —OR, where R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or substituted cycloheteroalkyl.

The term "alkylthio" denotes the group —SR, —S(O)$_{n=1-2}$—R, where R is lower alkyl, substituted lower alkyl, aryl, substituted aryl, arylalkyl or substituted arylalkyl.

The term "acyl" refers to groups —C(O)R, where R is hydrogen, lower alkyl, substituted lower alkyl, aryl, substituted aryl and the like.

The term "aryloxy" refers to groups —OAr, where Ar is an aryl, substituted aryl, heteroaryl, or substituted heteroaryl group.

The term "amino" refers to the group NRR', where R and R' may independently be hydrogen, lower alkyl, substituted lower alkyl, aryl, substituted aryl, heteroaryl, cycloalkyl, substituted heteroaryl, or acyl.

The term "amido" refers to the group —C(O)NRR', where R and R' may independently be hydrogen, lower alkyl, substituted lower alkyl, aryl, substituted aryl, heteroaryl, substituted heteroaryl.

The term "carboxyl" refers to the group —C(O)OR, where R may independently be hydrogen, lower alkyl, substituted lower alkyl, aryl, substituted aryl, heteroaryl, substituted heteroaryl and the like.

The terms "aryl" and "Ar" refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

The term "substituted aryl" refers to aryl optionally substituted with one or more functional groups, e.g., halogen, lower alkyl, lower alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O, or S, within the ring, which can optionally be unsubstituted or substituted with, e.g., halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

The term "heteroaryl" refers to a heterocycle in which at least one heterocyclic ring is aromatic.

The term "substituted heteroaryl" refers to a heterocycle optionally substituted with one or more substituents including halogen, lower alkyl, lower alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

The term "arylalkyl" refers to the group -R-Ar where Ar is an aryl group and R is lower alkyl or substituted lower alkyl group. Aryl groups can optionally be unsubstituted or substituted with, e.g., halogen, lower alkyl, alkoxy, alkylthio, trifluoromethyl, amino, amido, carboxyl, hydroxyl, aryl, aryloxy, heterocycle, heteroaryl, substituted heteroaryl, nitro, cyano, thiol, sulfamido and the like.

The term "heteroalkyl" refers to the group -R-Het where Het is a heterocycle group and R is a lower alkyl group. Heteroalkyl groups can optionally be unsubstituted or substituted with e.g., halogen, lower alkyl, lower alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

The term "heteroarylalkyl" refers to the group -R-HetAr where HetAr is a heteroaryl group and R is a lower alkyl or substituted lower alkyl. Heteroarylalkyl groups can optionally be unsubstituted or substituted with, e.g., halogen, lower alkyl, substituted lower alkyl, alkoxy, alkylthio, aryl, aryloxy, heterocycle, heteroaryl, substituted heteroaryl, nitro, cyano, alkylthio, thiol, sulfamido and the like.

The term "cycloalkyl" refers to a divalent cyclic or polycyclic alkyl group containing 3 to 15 carbons. For polycyclic groups, these may be multiple condensed rings in which one of the distal rings may be aromatic (e.g., indanyl, tetrahydronaphthalene, etc . . . ).

The term "substituted cycloalkyl" refers to a cycloalkyl group comprising one or more substituents with, e.g., halogen, lower alkyl, substituted lower alkyl, alkoxy, alkylthio, aryl, aryloxy, heterocycle, heteroaryl, substituted heteroaryl, nitro, cyano, alkylthio, thiol, sulfamido and the like.

The term "cycloheteroalkyl" refers to a cycloalkyl group wherein one or more of the ring carbon atoms is replaced with a heteroatom (e.g., N, O, S or P).

The term "substituted cycloheteroalkyl" refers to a cycloheteroalkyl group as herein defined which contains one or more substituents, such as halogen, lower alkyl, lower alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

The term "alkyl cycloalkyl" refers to the group -R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

It is within the knowledge of one skilled in the art that stereoisomers of the compositions described herein as well as isomer and stereoisomers of components that comprise the compositions identified herein all fall within the scope of compositions that are useful in the therapeutic method of this invention.

If the compound useful in the method of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. If the final compound contains an acidic group, cationic salts may be prepared. Typically the parent compound is treated with an excess of an alkaline reagent, such as hydroxide, carbonate or alkoxide, containing the appropriate cation. Cations such as $NA^+$, $K^+$, $Ca^{+2}$ and $NH^{4+}$ are examples of cations present in pharmaceutically acceptable salts.

Compounds of formula (I) may be prepared by the following process. The process is characterized by the reaction of compounds of the general formula:

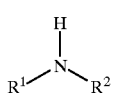

in which $R^1$ and $R^2$ have the meaning given above, with compounds of the general formula:

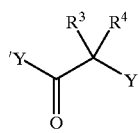

in which $R^3$ and $R^4$ have the meaning given above, and wherein 'Y represents halide, hydroxyl or O-acyl and wherein Y represents halide, preferably bromine. The reaction occurs in inert solvents and in the presence of base and/or auxiliaries, the later converted into compounds of the general formula:

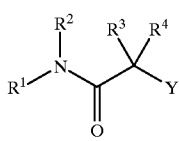

in which $R^1$, $R^2$, $R^3$, $R^4$ and Y have the meaning given above. These compounds are reacted with amines of the general formula $HR^5$ in which $R^5$ have the meanings given above, in inert solvents, and, if appropriate in the presence of base and/or auxiliaries.

The process according to the invention can be illustrated by way of example by the following reaction scheme:

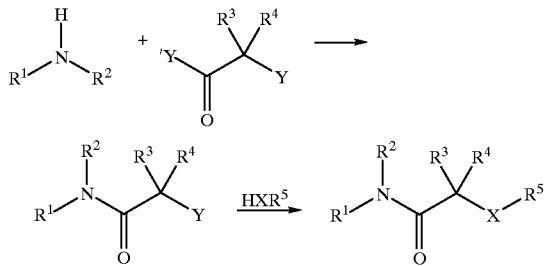

Suitable solvents for the process are customary organic solvents which do not change under the reaction conditions. These preferably include ethers such as diethyl ether, dioxane, tetrahydrofuran, glycol dimethyl ether, or alcohols, for example methanol, ethanol, propanol, isopropanol, butanol, iso-butanol or tert-butanol, or hydrocarbons such as benzene, toluene, xylene, hexane, cyclohexane or petroleum fractions, or halogenated hydrocarbons such as dichloromethane, trichloromethane, tetrachloromethane, dichloroethylene, trichloroethylene or chlorobenzene, or ethyl acetate, triethylamine, pyridine, dimethylsulphoxide, dimethylformamide, hexamethylphosphoramide, acetonitrile, acetone or nitromethane. It is also possible to use mixtures of the solvents mentioned. Dimethylformamide and dimethylsulphoxide are preferred.

Bases which can be employed for the process are in general inorganic or organic bases. These preferably include alkali metal hydroxides, for example sodium hydroxide or potassium hydroxide, alkaline earth metal hydroxides, for example barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl(C1–C6)-amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium or their hydrides such as sodium hydride. Potassium carbonate is preferred.

The above mentioned bases can, if appropriate, also be employed as acid-binding auxiliaries. Suitable auxiliaries are also dehydrating reagents. These include, for example, carbodiimides such as diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-19 oxazolium-3-sulphonate or propanephosphonic anhydride or iso-butyl chloroformate or benzotriazolyloxy-tris-(dimethylamino)phosphonium hexafluorophosphate or diphenyl phosphoramidate or methane-sulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids. In general, the base is employed in an amount from 0.05 to 10 mol, preferably from 1 to 2 mol, relative to 1 mol of the compound of this invention.

The processes for manufacturing compounds according to the invention are in general carried out in a temperature of from about −30° C. to about 110° C., preferably from about −10° C. to about 50° C. The manufacturing processes are in general carried out at normal pressure. However, it is also possible to carry out the processes at elevated pressure or at reduced pressure (e.g. in a range from 0.5 to 5 bar).

The compounds described above (some of which are disclosed in Tables 1–2 below) are useful for treating mammalian disorders such as eating disorders, obesity, hypertension, depression, brain or bodily disorders, and any other disorder mediated by NPY and the related Y5 receptor. It is preferred that the method of this invention is used to treat eating disorders such as obesity and bulimia. Specifically, the method of this invention can be used to inhibit the onset of obesity and to mediate the appetite in order to control and to reduce obese mammals such as humans. It is most preferred that the method of this invention is used to treat obesity and eating disorders in humans.

The compounds of the present invention are useful for treating disorders mediated by NPY via the Y5 receptor in mammals. For purposes of this disclosure, mammals includes humans, livestock, zoo animals, laboratory animals, experimental animals and pets. Livestock and related animals include, mammals such as cattle, horses, sheep, pigs, goats, camels, water buffaloes, donkeys, rabbits, fallow deer, reindeer; fur-bearing animals such as mink, chinchilla and raccoon; birds such as chickens, geese, turkeys and ducks. Laboratory animals and experimental animals include mice, rats, guinea pigs, golden hamsters, and pets include dogs, cats, rats, mice, guinea pigs, pigs, and the like.

The compounds of this invention may be administered to mammals both prophylactically and therapeutically by any administration protocol that is capable of supplying at least one compound of this invention to a Y5 receptor. Non-limiting examples of useful administration protocols include orally, parenterally, dermally, transdermally, rectally, nasally or by any other suitable pharmaceutical composition administration protocol that is within the knowledge of one skilled in the art.

The amide compositions of this invention will be administered in suitable pharmaceutical dosage forms. The pharmaceutical dosage form will depend largely upon the administration protocol used. The term pharmaceutical dosage form refers to items such as tablets, capsules, liquids and powders, comprising Y5 receptor inhibitors of this invention alone or in the presence of one or more pharmaceutical excipients. The choice of additives such as excipients and adjuvants again will depend largely upon the chosen administration protocol. The compounds of this invention can also be incorporated into food products such as biscuits and cookies. In essence, the compositions can be used as a dietary supplement to reduce or inhibit appetite. Those skilled in the pharmaceutical arts will recognize a wide variety of formulations and vehicles for administering compositions of this invention.

The administration protocol will largely dictate the final form and composition of pharmaceutical dosage forms comprising the Y5 receptor antagonists of this invention. For example, internal administration of compounds of this invention is effected, orally, in the form of powders, tablets, capsules, pastes, drinks, granules, or solutions, suspensions and emulsions which can be administered orally, or boli, in medicated food, or in drinking water. Internal administration may also be accomplished using a timed release formulation including additives such as surfactant or starch coated capsules, or using a quick release formulation such as a freeze-dried fast dissolving tablet. Dermal administration is effected, for example, in the form of transdermal patches, spraying or pouring-on and spotting-on. Parenteral administration is effected, for example, in the form of injection (intramuscularly, subcutaneously, intravenously, intraperitoneally) or by implants.

Suitable pharmaceutical dosage forms incorporating the Y5 receptor antagonists of this invention include but are not limited to solutions such as solutions for injection, oral solutions, concentrates for oral administration after dilution, solutions for use on the skin or in body cavities, pour-on and spot-on formulations, gels; emulsions and suspension for oral or dermal administration and for injection; semi-solid preparations; formulations in which the active compound is incorporated in cream base or in an oil-in-water or water-in-oil emulsion base; solid preparations such as powders, premixes or concentrates, granules, pellets, tablets, boli, capsules; aerosols and inhalants, and shaped articles containing active compound.

Pharmaceutical dosage forms that are solutions may be administered by injection intravenously, intramuscularly and subcutaneously. Solutions for injection are prepared by dissolving the active compound in a suitable solvent and, if appropriate, adding adjuvants such as solubilizers, acids, bases, buffer salts, antioxidants and preservatives. The solutions are sterile-filtered and drawn off.

Alternatively, solutions including compositions of this invention may be administered orally. Concentrates of compositions of this invention are preferably administered orally only after diluting the concentrate to the administration concentration. Oral solutions and concentrates are prepared as described above in the case of the solutions for injection. Solutions for use on the skin are applied dropwise, brushed on, rubbed in, splashed on or sprayed on. These solutions are prepared as described above in the case of solutions for injection.

Gels are applied to the skin, or introduced into body cavities. Gels are prepared by treating solutions which have been prepared as described in the case of the solutions for injection with such an amount of thickener that a clear substance of cream-like consistency is formed, or by any other means known to one skilled in the art.

Pour-on and spot-on formulations are poured onto, or splashed onto, limited areas of the skin, the active compound penetrating the skin and acting systemically. Pour-on and spot-on formulations are prepared by dissolving, suspending or emulsifying the active compound in suitable solvents or solvent mixtures which are tolerated by the skin. If appropriate, other adjuvants such as colorants, resorption accelerators, antioxidants, light stabilizers, and tackifiers are added.

Emulsions can be administered orally, dermally or in the form of injections. Emulsions are either of the water-in-oil type or of the oil-in-water type. They are prepared by dissolving Y5 receptor antagonists either in the hydrophobic or in the hydrophilic phase and homogenizing the phase with a solvent of the opposite phase with the aid of suitable adjuvants such as emulsifiers, colorants, resorption accelerators, preservatives, antioxidants, light stabilizers, and viscosity-increasing substances.

Suspensions can be administered orally, dermally or in the form of injection. They are prepared by suspending the active compound in a liquid if appropriate with the addition of further adjuvants such as wetting agents, colorants, resorption accelerators, preservatives, antioxidants and light stabilizers.

The pharmaceutical compositions of this invention may include one or more additives in the form of pharmaceutically acceptable additives. Useful additives include solvents, solubilizers, preservatives, thickeners, wetting agents, colorants, resorption accelerators, antioxidants, light stabilizers, tackifiers, viscosity increasing substances, fillers, flavorings, lubricating agents, and any other pharmaceutical composition additive known to those skilled in the art.

The additive may be a solvent such as water, alcohols such as ethanol, butanol, benzyl alcohol, glycerol, propylene glycol, polyethylene glycols, N-methyl-pyrrolidone, alkanols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol mono-methyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

The following additives may be useful as solubilizers of the compositions of this invention: solvents which enhance solution of the active compound in the main solvent or which prevent its precipitation. Examples are polyvinylpyrrolidone, polyoxyethylated castor oil, polyoxyethylated sorbitan esters.

Useful preservatives are, for example, benzyl alcohol, trichlorobutanol, p-hydroxybenzoic esters, and n-butanol.

Useful thickeners include inorganic thickeners such as bentonite, colloidal silica, aluminum monostearate, organic thickeners such as cellulose derivatives, polyvinyl alcohols and their copolymers, acrylates and methacrylates.

Other liquids which may be useful in pharmaceutical dosage forms of this invention are, for example, homogeneous solvents, solvent mixtures, and wetting agents (dispersants) which are typically surfactants.

Useful colorants are all colorants which are non-toxic and which can be dissolved or suspended.

Useful resorption accelerators are DMSO, spreading oils such as isopropyl myristate, dipropylene glycol pelargonate, silicone oils, fatty acid esters, triglycerides, fatty alcohols.

Useful antioxidants are sulphites or metabisulphites such as potassium metabisulphite, ascorbic acid, butylhydroxytoluene, butylhydroxyanisole, tocopherol.

A useful light stabilizer is novantisolic acid.

Useful tackifiers include cellulose derivatives, starch derivatives, polyacrylates, natural polymers such as alginates, gelatin.

Useful emulsifiers include non-ionic surfactants such as polyoxyethylated castor oil, polyoxyethylated sorbitan monooleate, sorbitan monostearate, glycerol monostearate, polyoxyethyl stearate, alkylphenol polyglycol ethers; ampholytic surfactants such as Di-Na N-lauryl- beta -iminodipropionate or lecithin; anionic surfactants, such as Na-lauryl sulphate, fatty alcohol ether sulphates, the monoethanolamine salt of mono/dialkylpolyglycol ether orthophosphoric esters; cationic surfactants such as cetyltrimethylammonium chloride.

Useful viscosity-increasing substances and substances which stabilize a therapeutic emulsion include carboxymethylcellulose, methylcellulose and other cellulose and starch derivatives, polyacrylates, alginates, gelatin, gum Arabic, polyvinylpyrrolidone, polyvinyl alcohol, copolymers of methyl vinyl ether and maleic anhydride, polyethylene glycols, waxes, colloidal silica or mixtures of the substances mentioned.

To prepare solid pharmaceutical dosage forms, the active compound is mixed with suitable additives, if appropriate with the addition of adjuvants, and the mixture is formulated as desired. Examples of physiologically acceptable solid inert additives include sodium chloride, carbonates such as calcium carbonate, hydrogen carbonates, aluminum oxides, silicas, clays, precipitated or colloidal silicon dioxide, and phosphates. Examples of solid organic additives include sugars, cellulose, foods such as dried milk, animal meals, cereal meals and coarse cereal meals and starches. Other suitable additives include lubricants and gliding agents such as magnesium stearate, stearic acid, talc, bentonites; disintegrants such as starch or crosslinked polyvinylpyrrolidone; binders such as, starch, gelatin or linear polyvinylpyrrolidone; and dry binders such as microcrystalline cellulose.

In the pharmaceutical dosage forms described herein, the active compounds can be present in the form of a mixture with at least one other Y5 receptor antagonist compound. Alternatively, or in addition, the pharmaceutical dosage forms of the invention can, in addition to at least one Y5 receptor antagonist, include any pharmaceutical compound that is capable of treating any known malady or disorder where the administration of both together create no unacceptable adverse effects.

Methods for treating NPY mediated diseases and disorders comprises the administration of an effective quantity of the chosen compound or combinations thereof, preferably dispersed in a pharmaceutical dosage form. Ready-to-use pharmaceutical dosage forms of this invention contain the active compound in concentrations of from 10 ppm to 20 per cent by weight, and preferably of from 0.1 to 10 per cent by weight. Pharmaceutical dosage forms of this invention that are diluted prior to administration, preferably contain the active compound in concentrations of from 0.5 to 90 per cent by weight, and preferably of from 5 to 50 per cent by weight.

In general, it has proved advantageous to administer amounts of approximately 0.01 mg to approximately 100 mg of active compound per kg of body weight per day to achieve effective results.

The amount and frequency of administration of pharmaceutical dosage forms comprising Y5 receptor antagonists of this invention will be readily determined by one skilled in the art depending upon, among other factors, the route of administration, age and condition of the patient. These dosage units may be administered one to ten times daily for acute or chronic disease. No unacceptable toxicological effects are expected when compounds of the invention are administered in accordance with the present invention.

The pharmaceutical dosage forms comprising Y5 receptor antagonists of this invention are made following the conventional techniques of pharmacy involving milling, mixing, granulation, and compressing, when necessary, for tablet forms; or milling, mixing and filling for hard gelatin capsule forms. When a liquid additive is used, the preparation will be in the form of a syrup, elixir, emulsion or an aqueous or non-aqueous suspension. Such a liquid formulation may be administered directly p.o. or filled into a soft gelatin capsule.

While the compositions described herein may be administered as described above, (i.e., intramuscular, intravenous and subcutaneous etc . . . ), it is preferred that the method of this invention is achieved by administering the compound described herein orally. When the oral administration route is chosen, a larger quantity of reactive agent will be required to produce the same effect as a smaller quantity given for example parenterally. In accordance with good clinical practice, it is preferred to administer the compound according to this method at a concentration level that would produce effective therapeutic results without causing any harmful side effects.

The compositions of this invention have non-therapeutic utility as well. The compositions of this invention are useful as analytical standards for Y5 receptor agonist or antagonist assays.

Compounds 1–329 identified in the Examples and in Tables 1 and 2 below are believed heretofore to be unknown. Known compounds that may be useful in the novel therapeutic method of this invention are compounds 330–3662 disclosed in Table 4 below.

EXAMPLES

The novel compounds useful in the therapeutic method of this invention are prepared by conventional methods of organic chemistry. Unless otherwise noted, reagents and solvents were obtained from commercial suppliers and were used without further purification.

The following solvent systems were used for analytical thin-layer chromatography (TLC): (A) ethyl acetate, (B) methylene chloride, (C) 9:1 dichloromethane:methanol, (D) 95:5 ethyl acetate:methanol, (E) 25:75 hexanes:ethyl acetate, (F) 7:3 hexanes:ethyl acetate, (G) 50:50 hexanes:ethyl acetate. TLC was performed on Merck Kieselgel 60 $F_{254}$ silica gel plates (solvent systems A, C, D, and E); or, Baker Reversed Phase Octadecyl ($C_{18}$) plates (solvent system B). Detection was effected by exposure to UV light (254 nm) or by immersion in basic aqueous potassium permanganate solution. Chromatography was performed using Silica Gel 60 (#9385-5) from EM Science.

Melting points were recorded in open capillary tubes and are uncorrected. $^1$H NMR spectra were determined at 300 MHz using a General Electric GE-OMEGA 300 spectrometer. Chemical shifts are reported in parts per million (d)

values relative to tetramethylsilane as internal standard. Spin multiplicities are reported using the following abbreviations: singlet (s), doublet (d), triplet (t), quartet (q), multiplet (m), and broad (br). Coupling constants are in Hertz.

Fast atom bombardment (FAB) mass spectra were recorded using a Kratos Concept 1 spectrometer; electron impact (EI) and chemical ionization (CI) mass spectra were recorded using a Hewlett-Packard MS Engine (HP5989A) spectrometer; liquid chromatography-mass spectra (LC-MS) were recorded using a Finningan MAT LCQ spectrometer.

Rainin high performance liquid chromatography (HPLC) systems with UV detectors at 254 nm were used under the following conditions: (N) $C_{18}$ Reversed Phase Cartridge Column (Perkin Elmer/PE Xpress #0258-0164); 20:80 (0.1:99.9 trifluoroacetic acid-acetonitrile)-(0.1:2:97.9 trifluoroacetic acid-acetonitrile-water) to 95:5 (0.1:99.9 trifluoroacetic acid-acetonitrile)-(0.1:2:97.9 trifluoroacetic acid-acetonitrile-water) over 8 minutes, 95:5 (0.1:99.9 trifluoroacetic acid-acetonitrile)-(0.1:2:97.9 trifluoroacetic acid-acetonitrile-water) for 2 minutes; 3 mL/min. (O) Rainin Microsorb 80-225-C5 $C_{18}$ Reversed Phase column with Microsorb 80-200-G5 $C_{18}$ Reversed Phase guard column; 50:50 (0.1:99.9 trifluoroacetic acid-acetonitrile)-(0.1:2:97.9 trifluoroacetic acid-acetonitrile-water) to 100:0 (0.1:99.9 trifluoroacetic acid-acetonitrile)-(0.1:2:97.9 trifluoroacetic acid-acetonitrile-water) over 5 minutes, 0.1:99.9 trifluoroacetic acid-acetonitrile for 5 minutes; 1 mL/min.

Example 1

Preparation of Intermediate -N-(4-Cyclohexyl-phenyl)-2-chloroacetamide:

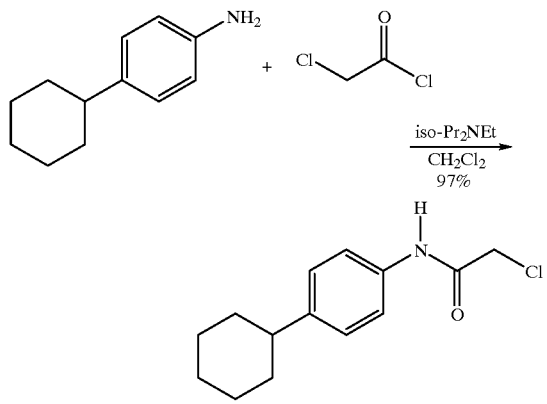

To 7.8 g (5.5 ml, 69.0 mmol) of chloroacetyl chloride in 200 ml of $CH_2Cl_2$ at 0° C., was added 12.0 g (69.0 mmol) of 4-cyclohexyaniline and 9.0 g (12.2 ml, 70.0 mmol). After warming to room temperature and stirring at room temperature for 1.5 hr, the reaction mixture was quenched with EtOAc. The organic layer was washed with 1N HCl, $H_2O$, and brine. The organic layer was separated and dried over $MgSO_4$, filtered and concentrated under reduced pressure to provide 16.8 g (97%) of the desired product. $^1H$ NMR (300 MHz, $CDCl_3$) d 8.20 (br s, 1H), 7.45 (d, 2H), 7.19 (d, 2H), 4.20 (s, 2H), 2.5 (br m, 1H), 1.95–1.70 (m, 4H), 1.45–1.2 (m, 4H). Using the same or analogous method, intermediates were prepared that were subsequently used according to the methods set forth in the Examples below to synthesize compounds of this invention.

Example 2

Compound 1: 2-(4-Benzyl-4-hydroxypiperidin-1-yl)-N-(4-cyclohexylphenyl)acetamide

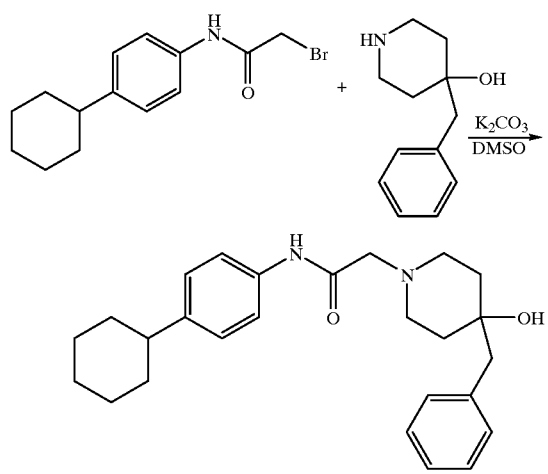

A mixture of N-(4-cyclohexyl-phenyl)-2-bromoacetamide (29.6 mg, 0.10 mmol), 4-benzyl-4-hydroxypiperidine (19.1 mg, 0.10 mmol), and potassium carbonate (13.8 mg, 0.1 mmol) in dimethyl sulfoxide (1.0 mL) was stirred 1 hour. The mixture was filtered through a short pad of Celite in a pasteur pipet. TLC $R_f$ 0.21 (silica gel, 50:50 hexane/ethyl acetate), 0.14 (reverse phase, 80:20 methanol/water); HPLC: 5.89 min (C18 Cartridge column (Perkin Elmer/PE Xpress #0258-0164) 20:80 Acetonitrile/water to 95:5 acetonitrile/water); LC-MS: 407 (M+H$^+$). The filtrate was tested directly in the in vitro biological assays.

The compounds of this invention that are set forth in Table 1, below, were prepared in analogy to the procedure of Example 2.

TABLE 1

| Compound | NAME | TLC | MS | HPLC |
|---|---|---|---|---|
| 2 | N-(4-Cyclohexyl-phenyl)-2-dimethylamino-acetamide | ND | ND | ND |
| 3 | 2-[4-(2-Chloro-phenyl)-piperazin-1-yl]-N-(4-cyclohexyl-phenyl)-acetamide | 0.74 (A), 0.83 (B) | 412 (M+H+, LC-MS) | 11.45 (O) |
| 4 | 2-[4-(4-Chloro-phenyl)-piperazin-1-yl]-N-(4-cyclohexyl-phenyl)-acetamide | 0.55 (A), 0.83 (B) | 412 (M+H+, LC-MS) | 12.53 (O) |
| 5 | N-(4-Benzoyl-phenyl)-2-(2,2-dimethoxy-ethylamino)-acetamide | 0.10 (A), 0.52 (B) | 343 (M+H+, LC-MS) | 5.03 (N) |
| 6 | N-(4-Benzoyl-phenyl)-2-morpholine-yl-acetamide | 0.15 (A), 0.56 (B) | 325 (M+H+, LC-MS) | 3.88 (O) |

TABLE 1-continued

| Compound | NAME | TLC | MS | HPLC |
|---|---|---|---|---|
| 7 | N-(4-Benzoyl-phenyl)-2-diethylamino-acetamide | 0.34 (A), 0.34 (B) | 311 (M+H+, LC-MS) | 4.42 (O) |
| 8 | N-(4-Benzoyl-phenyl)-2-[4-(2-chloro-phenyl)-piperazin-1-yl]-acetamide | 0.47 (A), 0.83 (B) | 434 (M+H+, LC-MS) | 8.62 (O) |
| 9 | N-(4-Benzoyl-phenyl)-2-[4-(3-chloro-phenyl)-piperazin-1-yl]-acetamide | 0.36 (A), 0.83 (B) | 434 (M+H+, LC-MS) | 8.71 (O) |
| 10 | N-(4-Benzoyl-phenyl)-2-[4-(4-chloro-phenyl)-piperazin-1-yl]-acetamide | 0.31 (A), 0.55 (B) | 434 (M+H+, LC-MS) | 8.68 (O) |
| 11 | 2-Benzylamino-N-(4-cyclohexyl-phenyl)-acetamide | ND | ND | ND |
| 12 | (4R,2S)-1-[(4-Cyclohexyl-phenylcarbamoyl)-methyl]-4-hydroxy-pyrrolidine-2-carboxylic acid | 0.31 (A), 0.41 (B) | 347 (M+H+, LC-MS) | 16.22 (O) |
| 13 | 2-(4-Benzyl-piperazin-1-yl)-N-(4-cyclohexyl-phenyl)-acetamide | 0.30 (A), 0.34 (B) | 392 (M+H+, LC-MS) | 5.48 (N) |
| 14 | N-(4-Cyclohexyl-phenyl)-2-[(2-hydroxy-ethyl)-phenyl-amino]-acetamide | 0.55 (A), 0.14 (B) | 403 (LC-MS) | 11.50 (O) |
| 15 | 2-[4-(4-Chloro-phenyl)-3,6-dihydro-2H-pyridin-1-yl]-N-(4-cyclohexyl-phenyl)-acetamide | 0.75 (A), 0.04 (B) | 407 (LC-MS) | 13.03 (O) |
| 16 | N-(4-Benzoyl-phenyl)-2-(4-benzyl-piperazin-1-yl)-acetamide | ND | ND | ND |
| 17 | N-(4-Benzoyl-phenyl)-2-[(2-hydroxy-ethyl)-phenyl-amino]-acetamide | ND | ND | ND |
| 18 | N-(4-Benzoyl-phenyl)-2-[4-(4-chloro-phenyl)-3,6-dihydro-2H-pyridin-1-yl]-acetamide | 0.41 (A), 0.15 (B) | 431 (M+H+, LC-MS) | 4.05 (O) |
| 19 | N-(4-Benzoyl-phenyl)-2-(4-benzyl-4-hydroxy-piperidin-1-yl)-acetamide | 0.15 (A), 0.34 (B) | 429 (M+H+, LC-MS) | 3.16 (N) |
| 20 | (5S,2R)-1-[(4-Benzoyl-phenylcarbamoyl)-methyl]-5-hydroxy-pyrrolidine-2-carboxylic acid | 0.15 (A), 0.38 (B) | 369 (M+H+, LC-MS) | 3.81 (N) |
| 21 | N-(4-Benzoyl-phenyl)-2-(ethyl-pyridin-4-ylmethyl-amino)-acetamide | ND | ND | ND |
| 22 | N-(4-Benzoyl-phenyl)-2-(di-pyridin-2-yl-amino)-acetamide | 0.34 (A), 0.45 (B) | 409 (M+H+, LC-MS) | ND |
| 23 | N-(4-Cyclohexyl-phenyl)-2-[4-(3-piperidine-4-yl-propyl)-piperidin-1-yl]-acetamide | 0.16 (A), 0.00 (B) | 352 (LC-MS) | 3.37 (N) |
| 24 | 2-[1,4']Bipiperidinyl-1'-yl-N-(4-cyclohexyl-phenyl)-acetamide | 0.70 (A), 0.10 (B) | 391 (LC-MS) | 2.79 (N) |
| 25 | 1-[(4-Cyclohexyl-phenylcarbamoyl)-methyl] piperidine-4-carboxylic acid | 0.16 (A), 0.15 (B) | 315 (LC-MS) | 4.04 (N) |
| 26 | N-(4-Cyclohexyl-phenyl)-2-(4-hydroxy-4-phenyl-piperidin-1-yl)-acetamide | 0.32 (A), 0.18 (B) | 393 (M+H+, LC-MS) | 4.12 (N) |
| 28 | N-(4-Cyclohexyl-phenyl)-2-[(piperidine-4-ylmethyl)-amino]-acetamide | 0.16 (A), 0.00 (B) | 384 (LC-MS) | 2.52 (N) |
| 29 | N-(4-Cyclohexyl-phenyl)-2-(4-pyrrolidin-1-yl-piperidin-1-yl)-acetamide | 0.16 (A), 0.10 (B) | 384 (LC-MS) | 2.67 (N) |
| 30 | 1-[(4-Cyclohexyl-phenylcarbamoyl)-methyl]-4-methylamino-piperidine-4-carboxylic acid amide | 0.16 (A), 0.30 (B) | 373 (M+H+, LC-MS) | 2.47 (N) |
| 31 | 1-[(4-Cyclohexyl-phenylcarbamoyl)-methyl]-4-phenylamino-piperidine-4-carboxylic acid amide | 0.16 (A), 0.25 (B) | 435 (M+H+, LC-MS) | 3.89 (N) |
| 32 | N-(4-Cyclohexyl-phenyl)-2-(4-dimethylamino-piperidin-1-yl)-acetamide | 0.10 (A), 0.10 (B) | 387 (LC-MS) | 4.93 (N) |
| 33 | N-(4-Cyclohexyl-phenyl)-2-(4-methyl-piperidin-1-yl)-acetamide | 0.20 (A), 0.06 (B) | 370 (LC-MS) | 6.32 (N) |
| 34 | N-(4-Cyclohexyl-phenyl)-2-(4,4-dimethyl-piperidin-1-yl)-acetamide | 0.65 (A), 0.10 (B) | 329 (M+H+, LC-MS) | 4.15 (N) |
| 35 | 4-Cyclohexylamino-1-[(4-cyclohexyl-phenylcarbamoyl)-methyl]-piperidine-4-carboxylic acid amide | 0.15 (A), 0.15 (B) | 441 (M+H+, LC-MS) | 2.91 (N) |
| 36 | 1-[(4-Cyclohexyl-phenylcarbamoyl)-methyl]-4-dimethylamino-piperidine-4-carboxylic acid amide | 0.08 (A), 0.31 (B) | 387 (M+H+, LC-MS) | 2.47 (N) |
| 37 | N-(4-Benzoyl-phenyl)-2-[4-(3-piperidin-4-yl-propyl)-piperidin-1-yl]-acetamide | 0.00 (A), 0.00 (B) | 380 (LC-MS) | 3.48 (N) |
| 38 | N-(4-Benzoyl-phenyl)-2-(4-benzyl-piperidin-1-yl)-acetamide | 0.69 (A), 0.00 (B) | 413 (M+H+, LC-MS) | 5.04 (N) |
| 39 | N-(4-Benzoyl-phenyl)-2-[1,4']bipiperidinyl-1'-yl-acetamide | 0.10 (A), 0.10 (B) | 366 (LC-MS) | 2.64 (N) |
| 40 | 1-[(Benzoyl-phenylcarbamoyl)-methyl]-piperidine-4-carboxylic acid | 0.28 (A) | 367 (M+H+, LC-MS) | 6.13 (N) |
| 41 | N-(4-Benzoyl-phenyl)-2-(4-hydroxy-4-phenyl-piperidin-1-yl)-acetamide | 0.28 (A), 0.15 (B) | 415 (M+H+, LC-MS) | 4.14 (N) |
| 42 | N-(4-Benzoyl-phenyl)-2-(4-hydroxy-piperidin-1-yl)-acetamide | 0.11 (A), 0.31 (B) | 339 (M+H+, LC-MS) | 2.94 (N) |
| 43 | N-(4-Benzoyl-phenyl)-2-[(piperidin-4-ylmethyl)-amino]-acetamide | 0.11 (A) | ND | 2.51 (N) |
| 44 | N-(4-Benzoyl-phenyl)-2-(4-cyano-4-phenyl- | 0.57 (A), | 476 (LC-MS) | 4.52 (N) |

TABLE 1-continued

| Compound | NAME | TLC | MS | HPLC |
|---|---|---|---|---|
|  | piperidin-1-yl)-acetamide | 0.12 (B) |  |  |
| 45 | N-(4-Benzoyl-phenyl)-2-(4-pyrrolidin-1-yl-piperidin-1-yl)-acetamide | ND | 352 (LC-MS) | 2.77 (N) |
| 46 | 1-[(4-Benzoyl-phenylcarbamoyl)-methyl]-4-methylamino-piperidine-4-carboxylic acid amide | 0.28 (B) | 395 (M+H+, LC-MS) | 2.38 (N) |
| 47 | 1-[(4-Benzoyl-phenylcarbamoyl)-methyl]-4-phenylamino-piperidine-4-carboxylic acid amide | 0.10 (A), 0.23 (B) | 457 (M+H+, LC-MS) | 3.80 (N) |
| 48 | 1-[(4-Benzoyl-phenylcarbamoyl)-methyl]-4-ethylamino-piperidine-4-carboxylic acid amide | 0.10 (A), 0.23 (B) | 409 (M+H+, LC-MS) | 2.49 (N) |
| 49 | N-(4-Benzoyl-phenyl)-2-(4-dimethylamino-piperidin-1-yl)-acetamide |  | 349 (LC-MS) | 3.22 (N) |
| 50 | N-(4-Benzoyl-phenyl)-2-(4-methyl-piperidin-1-yl)-acetamide | 0.57 (A), 0.07 (B) | 337 (M+H+, LC-MS) | 2.46 (N) |
| 51 | N-(4-Benzoyl-phenyl)-2-(4,4-dimethyl-piperidin-1-yl)-acetamide | 0.62 (A), 0.08 (B) | 351 (M+H+, LC-MS) | 4.21 (N) |
| 53 | 1-[(4-Benzoyl-phenylcarbamoyl)-methyl]-4-dimethylamino-piperidine-4-carboxylic acid amide | 0.26 (B) | 463 (LC-MS) | 2.49 (N) |
| 54 | N-(4-Cyclohexyl-phenyl)-2-[4-(2-piperidin-4-yl-ethyl)-piperidin-1-yl]-acetamide | 0.05 (A), 0.0.0 (B) | 387 (LC-MS) | 3.16 (N) |
| 55 | N-(4-Benzoyl-phenyl)-2-[4-(2-piperidin-4-yl-ethyl)-piperidin-1-yl]-acetamide | ND | 349 (LC-MS) | 1.82 (N) |
| 56 | 2-(4-(Acetylamino-methyl)-4-phenyl-piperidin-1-yl]-N-(4-benzoyl-phenyl)-acetamide | 0.10 (A), 0.42 (B) | 470 (M+H+, LC-MS) | 2.48 (N) |
| 57 | N-(4-Benzoyl-phenyl)-2-[4-(cyano-phenyl-methyl)-piperidin-1-yl]-acetamide | 0.29 (A), 0.28 (B) | 438 (M+H+, LC-MS) | 3.37 (N) |
| 58 | N-(4-Benzoyl-phenyl)-2-(4-oxo-1-phenyl-1,3,8-triaza-spiro[4.5]dec-8-yl)-acetamide | 0.07 (A), 0.28 (B) | 469 (M+H+, LC-MS) | 3.07 (N) |
| 59 | N-(4-Cyclohexyl-phenyl)-2-[4-(1-hydroxy-ethyl)-piperidin-1-yl]-acetamide | 0.16 (A), 0.20 (B) | 345 (M+H+, LC-MS) | 3.13 (N) |
| 60 | N-(4-Benzoyl-phenyl)-2-[4-hydroxy-4-(3-phenyl-propyl)-piperidin-1-yl]-acetamide | 0.12 (A), 0.25 (B) | 457 (M+H+, LC-MS) | 3.54 (N) |
| 61 | N-(4-Cyclohexyl-phenyl)-2-[4-hydroxy-4-(3-phenyl-propyl)-piperidin-1-yl]-acetamide | 0.23 (A), 0.10 (B) | 435 (M+H+, LC-MS) | 4.88 (N) |
| 62 | N-(4-Cyclohexyl-phenyl)-2-[4-hydroxy-4-(3-trifluoromethyl-phenyl)-piperidin-1-yl]-acetamide | 0.37 (A), 0.10 (B) | 435 (LC-MS) | 4.93 (N) |
| 63 | N-(4-Benzoyl-phenyl)-2-[4-hydroxy-4-(3-trifluoromethyl-phenyl)-piperidin-1-yl]-acetamide | 0.12 (A), 0.33 (B) | 483 (M+H+, LC-MS) | 3.77 (N) |
| 64 | 1-[(4-Benzoyl-phenylcarbamoyl)-methyl]-4-dimethylamino-piperidine-4-carboxylic acid amide | 0.00 (A), 0.53 (B) | 409 (M+H+, LC-MS) | 0.90 (N) |
| 65 | 1-[(4-Cyclohexyl-phenylcarbamoyl)-methyl]-4-dimethylamino-piperidine-4-carboxylic acid amide | 0.11 (A), 0.29 (B) | 387 (M+H+, LC-MS) | 2.46 (N) |
| 66 | N-(4-Benzoyl-phenyl)-2-(4-phenyl-4-propoxy-piperidin-1-yl)-acetamide | 0.54 (A), 0.10 (B) | 457 (M+H+, LC-MS) | 4.32 (N) |
| 67 | N-(4-Benzoyl-phenyl)-2-(4-{3-[1-(2-hydroxy ethyl)-piperidin-4-yl]-propyl}-piperidin-1-yl)-acetamide | 0.00 (A), 0.10 (B) | 492 (M+H+, LC-MS) | 1.96 (N) |
| 68 | N-(4-Cyclohexyl-phenyl)-2-(4-{3-[1-(2-hydroxy-ethyl)-piperidin-4-yl]-propyl}-piperidin-1-yl)-acetamide | 0.11 (A), 0.00 (B) | 470 (M+H+, LC-MS) | 3.44 (N) |
| 69 | N-(4-Benzoyl-phenyl)-2-(4-phenyl-4-propionyl-piperidin-1-yl)-acetamide | 0.46 (A), 0.28 (B) | 455 (M+H+, LC-MS) | 3.64 (N) |
| 70 | N-(4-Benzoyl-phenyl)-2-[4-(1-hydroxy-ethyl)-piperidin-1-yl]-acetamide | 0.10 (A), 0.47 (B) | 367 (M+H+, LC-MS) | 1.74 (N) |
| 71 | N-(4-Benzoyl-phenyl)-2-(4-hydroxy-4-p-tolyl-piperidin-1-yl)-acetamide | 0.20 (A), 0.37 (B) | 429 (M+H+, LC-MS) | 3.35 (N) |
| 72 | N-(4-Cyclohexyl-phenyl)-2-[4-phenyl-4-(piperidine-1-carbonyl)-piperidin-1-yl]-acetamide | 0.31 (A), 0.08 (B) | 488 (M+H+, LC-MS) | 5.68 (N) |
| 73 | N-(4-Benzoyl-phenyl)-2-[4-phenyl-4-(piperidine-1-carbonyl)-piperidin-1-yl]-acetamide | 0.20 (A), 0.24 (B) | 510 (M+H+, LC-MS) | 4.11 (N) |
| 74 | N-(4-Benzoyl-phenyl)-2-(4-butyryl-4-phenyl-piperidin-1-yl)-acetamide | 0.47 (A), 0.32 (B) | 469 (M+H+, LC-MS) | 4.27 (N) |
| 75 | 2-(4-Butyryl-4-phenyl-piperidin-1-yl)-N-(4-cyclohexyl-phenyl)-acetamide | 0.10 (A), 0.10 (B) | 448 (M+H+, LC-MS) | 2.64 (N) |
| 77 | N-(4-Benzoyl-phenyl)-2-(2-pyridin-3-yl-pyrrolidin-1-yl)-acetamide | 0.08 (A), 0.45 (B) | 386 (M+H+, LC-MS) | 1.52 (N) |
| 78 | N-(4-Benzoyl-phenyl)-2-(2S-pyrrolidin-1-ylmethyl-pyrrolidin-1-yl)-acetamide | 0.08 (A), 0.13 (B) | 392 (M+H+, LC-MS) | 1.59 (N) |
| 79 | N-(4-Cyclohexyl-phenyl)-2-(2S-pyrrolidin-1- | 0.28 (A), | 370 (M+H+, | 4.14 (N) |

TABLE 1-continued

| Compound | NAME | TLC | MS | HPLC |
|---|---|---|---|---|
| | ylmethyl-pyrrolidin-1-yl)-acetamide | 0.15 (B) | LC-MS) | |
| 80 | N-(4-Cyclohexyl-phenyl)-2-(3R-hydroxy-pyrrolidin-1-yl)-acetamide | 0.11 (A), 0.31 (B) | 303 (M+H+, LC-MS) | 2.94 (N) |
| 81 | N-(4-Benzoyl-phenyl)-2-(3R-hydroxy-pyrrolidin-1-yl)-acetamide | 0.08 (A), 0.58 (B) | 325 (M+H+, LC-MS) | 1.52 (N) |
| 82 | N-(4-Benzoyl-phenyl)-2-[2R-(hydroxy-diphenyl-methyl)-pyrrolidin-1-yl]-acetamide | 0.50 (A), 0.30 (B) | 491 (M+H+, LC-MS) | 4.16 (N) |
| 83 | N-(4-Cyclohexyl-phenyl)-2-[2R-(hydroxy-diphenyl-methyl)-pyrrolidin-1-yl]-acetamide | 0.11 (A) | 469 (M+H+, LC-MS) | 2.51 (N) |
| 84 | N-(4-Cyclohexyl-phenyl)-2-(2S-hydroxymethyl-pyrrolidin-1-yl)-acetamide | 0.57 (A), 0.12 (B) | 317 (M+H+, LC-MS) | 4.52 (N) |
| 85 | N-(4-Benzoyl-phenyl)-2-(2S-hydroxymethyl-pyrrolidin-1-yl)-acetamide | 0.13 (A), 0.53 (B) | 339 (M+H+, LC-MS) | 1.79 (N) |
| 86 | 2-(4-Acetyl-4-phenyl-piperidin-1-yl)-N-(4-benzoyl-phenyl)-acetamide | 0.30 (A), 0.33 (B) | 441 (M+H+, LC-MS) | 3.47 (N) |
| 87 | 2-(4-Acetyl-4-phenyl-piperidin-1-yl)-N-(4-cyclohexyl-phenyl)-acetamide | 0.45 (A), 0.10 (B) | 419 (M+H+, LC-MS) | 4.82 (N) |
| 88 | 2-[4-(4-Bromo-phenyl)-4-hydroxy-piperidin-1-yl]-N-(4-cyclohexyl-phenyl)-acetamide | 0.22 (A), 0.10 (B) | 472 (M+H+, LC-MS) | 4.79 (N) |
| 89 | N-(4-Benzoyl-phenyl)-2-[4-(4-bromo-phenyl)-4-hydroxy-piperidin-1-yl]-acetamide | 0.17 (A), 0.33 (B) | 494 (M+H+, LC-MS) | 3.58 (N) |
| 90 | (2R,4R)-1-[(4-Cyclohexyl-phenylcarbamoyl)-methyl]-4-hydroxy-pyrrolidine-2-carboxylic acid | 0.27 (A), 0.43 (B) | 329 (LC-MS) | 3.22 (N) |
| 91 | 2-(2S-Aminomethyl-pyrrolidin-1-yl)-N-(4-cyclohexyl-phenyl)-acetamide | 0.67 (A), 0.32 (B) | 176 (LC-MS) | 2.59 (N) |
| 92 | N-(4-Cyclohexyl-phenyl)-2-(3-hydroxy-pyrrolidin-1-yl)-acetamide | 0.12 (A), 0.32 (B) | 303 (M+H+, LC-MS) | 3.02 (N) |
| 93 | N-(4-Cyclohexyl-phenyl)-2-(2S-methoxymethyl-pyrrolidin-1-yl)-acetamide | 0.37 (A), 0.16 (B) | 331 (M+H+, LC-MS) | 3.91 (N) |
| 94 | N-(4-Cyclohexyl-phenyl)-2-((1S,5R)-1,3,3-trimethyl-6-aza-bicyclo[3.2.1]oct-6-yl)-acetamide | 0.72 (A), 0.12 (B) | 375 (LC-MS) | 5.47 (N) |
| 95 | (2S)-1-[(4-Cyclohexyl-phenylcarbamoyl)-methyl]-pyrrolidine-2-carboxylic acid benzyl ester | 0.27 (A), 0.33 (B) | 518 (LC-MS) | 4.80 (N) |
| 96 | (2S)-1-[(4-Cyclohexyl-phenylcarbamoyl)-methyl]-pyrrolidine-2-carboxylic acid methyl ester | 0.27 (A), 0.42 (B) | 234 (LC-MS) | 4.82 (N) |
| 97 | 2-(4-Bromo-piperidin-1-yl)-N-(4-cyclohexyl-phenyl)-acetamide | 0.58 (A), 0.12 (B) | 379 (M+, LC-MS) | 4.12 (N) |
| 98 | (2S,4R)-1-[(4-Cyclohexyl-phenylcarbamoyl)-methyl]-4-hydroxy-pyrrolidine-2-carboxylic acid | 0.30 (A), 0.42 (B) | 347 (M+H+, LC-MS) | 6.24 (N) |
| 99 | (2S)-1-[(4-Cyclohexyl-phenylcarbamoyl)-methyl]-pyrrolidine-2-carboxylic acid | 0.23 (A), 0.42 (B) | 331 (M+H+, LC-MS) | 6.63 (N) |
| 100 | 2-(3-Amino-pyrrolidin-1-yl)-N-(4-cyclohexyl-phenyl)-acetamide | 0.25 (A), 0.08 (B) | 302 (M+H+, LC-MS) | 4.83 (N) |
| 101 | (2R,4R)-1-[(4-Benzoyl-phenylcarbamoyl)-methyl]-4-hydroxy-pyrrolidine-2-carboxylic acid | 0.15 (A), 0.62 (B) | 351 (LC-MS) | 3.81 (N) |
| 103 | N-(4-Benzoyl-phenyl)-2-(3-hydroxy-pyrrolidin-1-yl)-acetamide | 0.06 (A), 0.49 (B) | 325 (M+H+, LC-MS) | 1.52 (N) |
| 104 | N-(4-Benzoyl-phenyl)-2-(2S-methoxymethyl-pyrrolidin-1-yl)-acetamide | 0.25 (A), 0.32 (B) | 353 (M+H+, LC-MS) | 2.36 (N) |
| 105 | N-(4-Benzoyl-phenyl)-2-((1S,5R)-1,3,3-trimethyl-6-aza-bicyclo[3.2.1]oct-6-yl)-acetamide | 0.69 (A), 0.06 (B) | 391 (M+H+, LC-MS) | 3.83 (N) |
| 106 | (2S)-1-[(4-Benzoyl-phenylcarbamoyl)-methyl]-pyrrolidine-2-carboxylic acid benzyl ester | 0.43 (A), 0.60 (B) | 443 (M+H+, LC-MS) | 3.22 (N) |
| 107 | (2S)-1-[(4-Benzoyl-phenylcarbamoyl)-methyl]-pyrrolidine-2-carboxylic acid methyl ester | ND LC-MS) | 367 (M+H+, | 3.22 (N) |
| 108 | N-(4-Benzoyl-phenyl)-2-(4-bromo-piperidin-1-yl)-acetamide | 0.35 (A), 0.25 (B) | 401 (M+, LC-MS) | 2.61 (N) |
| 109 | (2S,4R)-1-[(4-Benzoyl-phenylcarbamoyl)-methyl]-4-hydroxy-pyrrolidine-2-carboxylic acid | 0.12 (A), 0.32 (B) | 369 (M+H+, LC-MS) | 3.82 (N) |
| 110 | (2S)-1-[(4-Benzoyl-phenylcarbamoyl)-methyl]-pyrrolidine-2-carboxylic acid | 0.12 (A), 0.78 (B) | 353 (M+H+, LC-MS) | 4.67 (N) |
| 111 | N-(4-Benzoyl-phenyl)-2-(4-benzyl-4-hydroxy-piperidin-1-yl)-acetamide | 0.12 (A), 0.29 (B) | 429 (M+H+, LC-MS) | 3.11 (N) |
| 112 | 2-(3-Amino-pyrrolidin-1-yl)-N-(4-benzoyl-phenyl)-acetamide | 0.10 (A), 0.06 (B) | 324 (M+H+, LC-MS) | 3.56 (N) |
| 113 | N-(4-Cyclohexyl-phenyl)-2-(2R-hydroxymethyl-pyrrolidin-1-yl)-acetamide | 0.15 (A), 0.23 (B) | 317 (M+H+, LC-MS) | 3.30 (N) |
| 114 | 1-[(4-Cyclohexyl-phenylcarbamoyl)-methyl]-2,2,5,5-tetramethyl-pyrrolidine-3-carboxylic acid amide | 0.17 (A), 0.20 (B) | 387 (M+H+, LC-MS) | 3.84 (N) |
| 115 | (2S,3R,4R)-3-Carboxymethyl-1-[(4-cyclohexyl-phenylcarbamoyl)-methyl]-4-isopropenyl-pyrrolidine-2-carboxylic acid | 0.24 (A), 0.36 (B) | 429 (M+H+, LC-MS) | 3.82 (N) |

TABLE 1-continued

| Compound | NAME | TLC | MS | HPLC |
|---|---|---|---|---|
| 116 | N-(4-Cyclohexyl-phenyl)-2-[4-(4-methoxy-benzoyl)-piperidin-1-yl]-acetamide | 0.24 (A), 0.33 (B) | 423 (LC-MS) | 4.00 (N) |
| 117 | (2R)-1-[(4-Cyclohexyl-phenylcarbamoyl)-methyl]-pyrrolidine-2-carboxylic acid | 0.05 (A), 0.37 (B) | 331 (M+H+, LC-MS) | 3.62 (N) |
| 118 | N-(4-Benzoyl-phenyl)-2-(2-hydroxymethyl-pyrrolidin-1-yl)-acetamide | 0.13 (A), 0.47 (B) | 339 (M+H+, LC-MS) | 1.72 (N) |
| 119 | 1-[(4-Benzoyl-phenylcarbamoyl)-methyl]-2,2,5,5-tetramethyl-pyrrolidine-3-carboxylic acid amide | 0.15 (A), 0.43 (B) | 408 (M+H+, LC-MS) | 2.33 (N) |
| 120 | 1-[(4-Benzoyl-phenylcarbamoyl)-methyl]-3-carboxymethyl-4-isopropenyl-pyrrolidine-2-carboxylic acid | 0.15 (A), 0.24 (B) | 451 (M+H+, LC-MS) | 6.14 (N) |
| 121 | N-(4-Benzoyl-phenyl)-2-[4-(4-fluoro-benzoyl)-piperidin-1-yl]-acetamide | 0.30 (A), 0.24 (B) | 445 (M+H+, LC-MS) | 3.54 (N) |
| 122 | N-(4-Benzoyl-phenyl)-2-[4-(4-methoxy-benzoyl)-piperidin-1-yl]-acetamide | 0.15 (A), 0.60 (B) | 515 (LC-MS) | 2.69 (N) |
| 123 | 1-[(4-Benzoyl-phenylcarbamoyl)-methyl]-pyrrolidine-2-carboxylic acid amide | 0.13 (A), 0.56 (B) | 352 (M+H+, LC-MS) | 1.58 (N) |
| 124 | 1-[(4-Benzoyl-phenylcarbamoyl)-methyl]-pyrrolidine-2-carboxylic acid | 0.13 (A), 0.64 (B) | 353 (M+H+, LC-MS) | 2.47 (N) |
| 125 | N-(4-Benzoyl-phenyl)-2-[2-(hydroxy-diphenyl-methyl)-pyrrolidin-1-yl]-acetamide | 0.57 (A), 0.20 (B) | 491 (M+H+, LC-MS) | 4.20(N) |
| 126 | N-(4-Cyclohexyl-phenyl)-2-[4-iodo-4-(2-iodo-ethyl)-piperidin-1-yl]-acetamide | 0.63 (A), 0.14 (B) | 561 (M+H+, LC-MS) | 4.98 (N) |
| 128 | 2-[4-(4-Chloro-benzoyl)-piperidin-1-yl]-N-(4-cyclohexyl-phenyl)-acetamide | 0.40 (A), 0.10 (B) | 439 (M+H+, LC-MS) | 5.21 (N) |
| 129 | N-(4-Cyclohexyl-phenyl)-2-pyrrolidin-1-yl-acetamide | ND | ND | ND |
| 130 | N-(4-Cyclohexyl-phenyl)-2-(1H-[1,2,4]triazol-3-ylamino)-acetamide | 0.18 (A), 0.45 (B) | 373 (LC-MS) | 3.21 (N) |
| 131 | 2-(Benzhydryl-amino)-N-(4-cyclohexyl-phenyl)-acetamide | 0.23 (A), 0.12 (B) | 399 (M+H+, LC-MS) | 5.24 (N) |
| 132 | N-(4-Cyclohexyl-phenyl)-2-[2-(1-methyl-1H-pyrrol-2-yl)-ethylamino]-acetamide | 0.22 (A), 0.38 (B) | 340 (M+H+, LC-MS) | 7.79 (N) |
| 133 | N-(4-Benzoyl-phenyl)-2-[4-iodo-4-(2-iodo-ethyl)-piperidin-1-yl]-acetamide | 0.47 (A), 0.34 (B) | 603 (M+H+, LC-MS) | 3.46 (N) |
| 134 | 2-{4-[(2-Amino-ethylamino)-methyl]-piperidin-1-yl}-N-(4-benzoyl-phenyl)-acetamide | 0.03 (A), 0.31 (B) | 395 (M+H+, LC-MS) | 1.13 (N) |
| 135 | N-(4-Benzoyl-phenyl)-2-[4-(4-chloro-benzoyl)-piperidin-1-yl]-acetamide | 0.28 (A), 0.21 (B) | 461 (M+H+, LC-MS) | 3.93 (N) |
| 136 | N-(4-Benzoyl-phenyl)-2-pyrrolidin-1-yl-acetamide | ND | ND | ND |
| 137 | N-(4-Benzoyl-phenyl)-2-(1H-[1,2,4]triazol-3-ylamino)-acetamide | 0.12 (A), 0.69 (B) | 322 (M+H+, LC-MS) | 1.93 (N) |
| 138 | 2-(Benzhydryl-amino)-N-(4-benzoyl-phenyl)-acetamide | 0.43 (A), 0.23 (B) | 421 (M+H+, LC-MS) | 4.00 (N) |
| 139 | N-(4-Benzoyl-phenyl)-2-[2-(1-methyl-1H-pyrrol-2-yl)-ethylamino]-acetamide | 0.10 (A), 0.12 (B) | 362 (M+H+, LC-MS) | 5.31 (N) |
| 140 | N-(4-Cyclohexyl-phenyl)-2-decylamino-acetamide | 0.14 (A), 0.10 (B) | ND | 6.40 (N) |
| 141 | N-(4-Cyclohexyl-phenyl)-2-(3-phenyl-propylamino)-acetamide | 0.14 (A), 0.10 (B) | 351 (M+H+, LC-MS) | 6.29 (N) |
| 142 | N-(4-Cyclohexyl-phenyl)-2-[2-(1H-imidazol-4-yl)-ethylamino]-acetamide | 0.10 (B) | 351 (LC-MS) | 7.80 (N) |
| 143 | N-(4-Cyclohexyl-phenyl)-2-[2-(1H-indol-3-yl)-ethylamino]-acetamide | 0.08 (A), 0.12 (B) | 376 (M+H+, LC-MS) | 6.05 (N) |
| 144 | N-(4-Cyclohexyl-phenyl)-2-[2-(5-methoxy-1H-indol-3-yl)-ethylamino]-acetamide | 0.08 (A), 0.14 (B) | 406 (M+H+, LC-MS) | 6.69 (N) |
| 145 | N-(4-Cyclohexyl-phenyl)-2-[2-(4-methoxy-phenyl)-ethylamino]-acetamide | 0.12 (A), 0.10 (B) | 367 (M+H+, LC-MS) | ND |
| 146 | N-(4-Cyclohexyl-phenyl)-2-(2-piperazin-1-yl-ethylamino)-acetamide | 0.06 (A) | 345 (M+H+, LC-MS) | 3.50 (N) |
| 147 | N-(4-Cyclohexyl-phenyl)-2-[2-(5-nitro-pyridin-2-ylamino)-ethylamino]-acetamide | 0.06 (A) | 398 (M+H+, LC-MS) | 9.52 (N) |
| 148 | 2-[(Benzo[1,3]dioxol-5-ylmethyl)-amino]-N-(4-cyclohexyl-phenyl)-acetamide | 0.14 (A), 0.13 (B) | 367 (M+H+, LC-MS) | 5.53 (N) |
| 149 | N-(4-Cyclohexyl-phenyl)-2-(2-methoxy-benzylamino)-acetamide | 0.14 (A), 0.11 (B) | 353 (M+H+, LC-MS) | 5.85 (N) |
| 150 | N-(4-Benzoyl-phenyl)-2-decylamino-acetamide | 0.23 (A), 0.58 (B) | ND | 4.45 (N) |
| 151 | N-(4-Benzoyl-phenyl)-2-(3-phenyl-propylamino)-acetamide | 0.30 (A), 0.22 (B) | 373 (M+H+, LC-MS) | 7.20 (N) |
| 152 | N-(4-Benzoyl-phenyl)-2-[2-(1H-imidazol-4-yl)-ethylamino]-acetamide | 0.23 (B) | 349 (M+H+, LC-MS) | 5.10 (N) |
| 153 | N-(4-Benzoyl-phenyl)-2-[2-(1H-indol-3-yl)-ethylamino]-acetamide | 0.23 (A), 0.12 (B) | 398 (M+H+, LC-MS) | 6.81 (N) |
| 155 | N-(4-Benzoyl-phenyl)-2-[2-(4-methoxy-phenyl)- | 0.27 (A), | 389 (M+H+, | 6.93 (N) |

TABLE 1-continued

| Compound | NAME | TLC | MS | HPLC |
|---|---|---|---|---|
| | ethylamino]-acetamide | 0.22 (B) | LC-MS) | |
| 156 | N-(4-Benzoyl-phenyl)-2-(2-piperazin-1-yl-ethylamino)-acetamide | 0.07 (A), 0.07 (B) | 367 (M+H+, LC-MS) | 2.07 (N) |
| 157 | N-(4-Benzoyl-phenyl)-2-[2-(5-nitro-pyridin-2-ylamino)-ethylamino]-acetamide | 0.10 (A), 0.37 (B) | 420 (M+H+, LC-MS) | 6.32 (N) |
| 158 | 2-[(Benzo[1,3]dioxol-5-ylmethyl)-amino]-N-(4-benzoyl-phenyl)-acetamide | 0.17 (A), 0.31 (B) | 389 (M+H+, LC-MS) | 9.69 (N) |
| 159 | N-(4-Benzoyl-phenyl)-2-(2-methoxy-benzylamino)-acetamide | 0.17 (A), 0.31 (B) | 375 (M+H+, LC-MS) | 5.70 (N) |
| 160 | N-(4-Cyclohexyl-phenyl)-2-[(furan-2-ylmethyl)-amino]-acetamide | 0.37 (A), 0.22 (B) | 313 (M+H+, LC-MS) | 9.07 (N) |
| 161 | 2-(2-Chloro-6-phenoxy-benzylamino)-N-(4-cyclohexyl-phenyl)-acetamide | 0.66 (A), 0.06 (B) | 448 (M+, LC-MS) | 6.86 (N) |
| 162 | 2-(Benzo[1,2,5]thiadiazol-4-ylamino)-N-(4-cyclohexyl-phenyl)-acetamide | 0.74 (A), 0.11 (B) | 367 (M+H+, LC-MS) | 0.95 (N) |
| 163 | N-(4-Cyclohexyl-phenyl)-2-phenethylamino-acetamide | 0.31 (A), 0.11 (B) | 337 (M+H+, LC-MS) | 9.57 (N) |
| 164 | N-(4-Cyclohexyl-phenyl)-2-(2,6-diiodo-4-nitro-phenylamino)-acetamide | 0.22 (A), 0.06 (B) | 337 (LC-MS) | 4.97 (N) |
| 165 | 4-{[(4-Cyclohexyl-phenylcarbamoyl)-methyl]-amino}-3,5-diiodo-benzoic acid anion | 0.56 (A), 0.11 (B) | 603 (M+H+, LC-MS) | 7.95 (N) |
| 166 | N-(4-Benzoyl-phenyl)-2-[(furan-2-yl-methyl)-amino]-acetamide | 0.12 (A), 0.22 (B) | 335 (M+H+, LC-MS) | 6.02 (N) |
| 167 | N-(4-Benzoyl-phenyl)-2-(2-chloro-6-phenoxy-benzylamino)-acetamide | 0.31 (A), 0.16 (B) | 471 (M+H+, LC-MS) | 7.90 (N) |
| 168 | 2-(Benzo[1,2,5]thiadiazol-4-ylamino)-N-(4-benzoyl-phenyl)-acetamide | 0.46 (A), 0.33 (B) | 389 (M+H+, LC-MS) | 0.93 (N) |
| 169 | N-(4-Benzoyl-phenyl)-2-phenethylamino-acetamide | 0.11 (A), 0.11 (B) | 359 (M+H+, LC-MS) | 6.23 (N) |
| 170 | N-(4-Benzoyl-phenyl)-2-(2,6-diiodo-4-nitro-phenylamino)-acetamide | 0.15 (A), 0.24 (B) | 359 (LC-MS) | 4.79 (N) |
| 171 | 4{[(4-Benzoyl-phenylcarbamoyl)-methyl]-amino}-3,5-diiodo-benzoic acid | 0.45 (A), 0.24 (B) | 627 (M+H+, LC-MS) | 6.16 (N) |
| 172 | N-(4-Cyclohexyl-phenyl)-2-cyclopropylamino-acetamide | 0.24 (A), 0.19 (B) | 317 (LC-MS) | 4.48 (N) |
| 173 | N-(4-Cyclohexyl-phenyl)-2-(2-hydroxy-1-hydroxymethyl-ethylamino)-acetamide | 0.10 (A), 0.30 (B) | 307 (M+H+, LC-MS) | 2.91 (N) |
| 174 | N-(4-Cyclohexyl-phenyl)-2-(cyclopropylmethyl-amino)-acetamide | 0.24 (A), 0.10 (B) | 488 (LC-MS) | 7.80 (N) |
| 175 | N-(4-Cyclohexyl-phenyl)-2-[3-(4-methyl-piperazin-1-yl)-propylamino]-acetamide | 0.10 (A), 0.10 (B) | 287 (LC-MS) | 2.58 (N) |
| 176 | N-(4-Cyclohexyl-phenyl)-2-(2-hydroxy-ethylamino)-acetamide | 0.10 (A), 0.23 (B) | 277 (M+H+, LC-MS) | 2.95 (N) |
| 177 | N-(4-Cyclohexyl-phenyl)-2-(2-hydroxy-1-hydroxymethyl-1-methyl-ethylamino)-acetamide | 0.10 (A), 0.28 (B) | 321 (M+H+, LC-MS) | 3.07 (N) |
| 178 | N-(4-Cyclohexyl-phenyl)-2-(3-pyrrolidin-1-yl-propylamino)-acetamide | 0.10 (A), 0.05 (B) | 373 (M+H+, LC-MS) | 2.77 (N) |
| 179 | N-(4-Cyclohexyl-phenyl)-2-(3-oxo-cyclohex-1-enylamino)-acetamide | 0.22 (A), 0.21 (B) | 327 (M+H+, LC-MS) | 0.23 (N) |
| 180 | 3-{[(4-Cyclohexyl-phenylcarbamoyl)-methyl]-amino}-4,4,4-trifluoro-butyric acid | 0.42 (A), 0.23 (B) | 373 (M+H+, LC-MS) | 3.69 (N) |
| 182 | N-(4-Benzoyl-phenyl)-2-cyclopropylamino-acetamide | 0.14 (A), 0.19 (B) | 344 (LC-MS) | 4.61 (N) |
| 183 | N-(4-Benzoyl-phenyl)-2-(2-hydroxy-1-hydroxymethyl-ethylamino)-acetamide | 0.56 (B) | 329 (M+H+, LC-MS) | 1.40 (N) |
| 184 | N-(4-Benzoyl-phenyl)-2-(cyclopropylmethyl-amino)-acetamide | 0.13 (A), 0.21 (B) | 309 (M+H+, LC-MS) | 4.94 (N) |
| 185 | N-(4-Benzoyl-phenyl)-2-[3-(4-methyl-piperazin-1-yl)-propylamino]-acetamide | 0.10 (B) | 395 (M+H+, LC-MS) | 1.23 (N) |
| 186 | N-(4-Benzoyl-phenyl)-2-(2-hydroxy-ethylamino)-acetamide | 0.25 (B) | 299 (M+H+, LC-MS) | 1.41 (N) |
| 187 | N-(4-Benzoyl-phenyl)-2-(2-hydroxy-1-hydroxymethyl-1-methyl-ethylamino)-acetamide | 0.15 (A), 0.56 (B) | 343 (M+H+, LC-MS) | 2.04 (N) |
| 188 | N-(4-Benzoyl-phenyl)-2-(3-pyrrolidin-1-yl-propylamino)-acetamide | | 366 (M+H+, LC-MS) | 1.42 (N) |
| 189 | N-(4-Benzoyl-phenyl)-2-(3-oxo-cyclohex-1-enylamino)-acetamide | 0.14 (A), 0.51 (B) | 366 (LC-MS) | 4.61 (N) |
| 190 | 3-{[(4-Benzoyl-phenylcarbamoyl)-methyl]-amino}-4,4,4-trifluoro-butyric acid | 0.25 (A), 0.41 (B) | 395 (M+H+, LC-MS) | 2.41 (N) |
| 191 | N-(4-Benzoyl-phenyl)-2-[2-(4-fluoro-phenyl)-1,1-dimethyl-ethylamino]-acetamide | 0.60 (A), 0.41 (B) | 405 (M+H+, LC-MS) | 4.99 (N) |
| 192 | N-(4-Cyclohexyl-phenyl)-2-[2-(4-hydroxy-3-methoxy-phenyl)-ethylamino]-acetamide | 0.20 (A), 0.42 (B) | 383 (M+H+, LC-MS) | 3.23 (N) |
| 193 | N-(4-Cyclohexyl-phenyl)-2-(3-methylamino-pyrrolidin-1-yl)-acetamide | 0.05 (A), 0.24 (B) | 598 (LC-MS) | 2.64 (N) |

TABLE 1-continued

| Compound | NAME | TLC | MS | HPLC |
|---|---|---|---|---|
| 194 | {1-[(4-Cyclohexyl-phenylcarbamoyl)-methyl]-pyrrolidin-3-yl}-carbamic acid tert-butyl ester | 0.28 (A) | 402 (M+H+, LC-MS) | 4.67 (N) |
| 195 | {1-[(4-Cyclohexyl-phenylcarbamoyl)-methyl]-pyrrolidin-3-yl}-carbamic acid tert-butyl ester | 0.28 (A), 0.18 (B) | 402 (M+H+, LC-MS) | 4.52 (N) |
| 196 | N-(4-Cyclohexyl-phenyl)-2-(3-ethylamino-pyrrolidin-1-yl)-acetamide | 0.13 (A) | 346 (LC-MS) | 2.68 (N) |
| 197 | N-{1-[(4-Cyclohexyl-phenylcarbamoyl)-methyl]-pyrrolidin-3-yl}-2,2,2-trifluoro-acetamide | 0.20 (A), 0.25 (B) | 398 (M+H+, LC-MS) | 4.14 (N) |
| 198 | N-(4-Cyclohexyl-phenyl)-2-(3-methylamino-pyrrolidin-1-yl)-acetamide | 0.12 (B) | 302 (LC-MS) | 2.60 (N) |
| 199 | N-(4-Cyclohexyl-phenyl)-2-(3-ethylamino-pyrrolidin-1-yl)-acetamide | 0.10 (A), 0.10 (B) | 330 (M+H+, LC-MS) | 2.67 (N) |
| 200 | N-(4-Cyclohexyl-phenyl)-2-(4-hydroxymethyl-piperidin-1-yl)-acetamide | 0.10 (A), 0.26 (B) | 331 (M+H+, LC-MS) | 3.10 (N) |
| 201 | 2-(Cyanomethyl-amino)-N-(4-cyclohexyl-phenyl)-acetamide | 0.23 (A), 0.38 (B) | 272 (M+H+, LC-MS) | 4.11 (N) |
| 202 | N-(4-Benzoyl-phenyl)-2-[2-(4-hydroxy-3-methoxy-phenyl)-ethylamino]-acetamide | 0.14 (A), 0.68 (B) | 368 (LC-MS) | 3.21 (N) |
| 203 | N-(4-Benzoyl-phenyl)-2-(3-methylamino-pyrrolidin-1-yl)-acetamide | 0.05 (A), 0.22 (B) | 338 (M+H+, LC-MS) | 3.55 (N) |
| 204 | {1-[(4-Benzoyl-phenylcarbamoyl)-methyl)-pyrrolidin-3-yl}-carbamic acid tert-butyl ester | 0.14 (A), 0.63 (B) | 424 (M+H+, LC-MS) | 4.86 (N) |
| 205 | {1-[(4-Benzoyl-phenylcarbamoyl)-methyl]-pyrrolidin-3-yl}-carbamic acid tert-butyl ester | 0.14 (A), 0.37 (B) | 424 (M+H+, LC-MS) | 3.23 (N) |
| 206 | N-(4-Benzoyl-phenyl)-2-(3-ethylamino-pyrrolidin-1-yl)-acetamide | 0.10 (B) | 352 (M+H+, LC-MS) | 1.28 (N) |
| 207 | N-{1-[(4-Benzoyl-phenylcarbamoyl)-methyl]-pyrrolidin-3-yl}-2,2,2-trifluoro-acetamide | 0.10 (A), 0.48 (B) | 420 (M+H+, LC-MS) | 2.75 (N) |
| 208 | N-(4-Benzoyl-phenyl)-2-(3-methylamino-pyrrolidin-1-yl)-acetamide | 0.05 (A), 0.10 (B) | 338 (M+H+, LC-MS) | 1.21 (N) |
| 209 | N-(4-Benzoyl-phenyl)-2-(3-ethylamino-pyrrolidin-1-yl)-acetamide | 0.05 (A), 0.10 (B) | 352 (M+H+, LC-MS) | 1.37 (N) |
| 210 | N-(4-Benzoyl-phenyl)-2-(4-hydroxymethyl-piperidin-1-yl)-acetamide | 0.10 (A), 0.49 (B) | 353 (M+H+, LC-MS) | 1.68 (N) |
| 211 | N-(4-Benzoyl-phenyl)-2-(cyanomethyl-amino)-acetamide | 0.49 (A), 0.60 (B) | 294 (M+H+, LC-MS) | 1.91 (N) |
| 212 | 4-({[(4-Cyclohexyl-phenylcarbamoyl)-methyl]-amino}-methyl)-benzoic acid | 0.28 (A), 0.39 (B) | 367 (M+H+, LC-MS) | 5.04 (N) |
| 213 | N-(4-Cyclohexyl-phenyl)-2-(1,1-dimethyl-prop-2-ynylamino)-acetamide | 0.59 (A), 0.25 (B) | 299 (M+H+, LC-MS) | 3.67 (N) |
| 214 | 2-(Cyclohexylmethyl-amino)-N-(4-cylohexyl-phenyl)-acetamide | 0.28 (A), 0.05 (B) | 329 (M+H+, LC-MS) | 4.91 (N) |
| 215 | {1-[(4-Cyclohexyl-phenylcarbamoyl)-methyl]-pyrrolidin-3-yl}-methyl-carbamic acid tert-butyl ester | 0.30 (A), 0.14 (B) | 416 (M+H+, LC-MS) | 5.39 (N) |
| 216 | N-(4-Cyclohexyl-phenyl)-2-(1-hydroxymethyl-butylamino)-acetamide | 0.28 (A), 0.22 (B) | 319 (M+H+, LC-MS) | 7.64 (N) |
| 217 | N-(4-Cyclohexyl-phenyl)-2-(4-hydroxy-butylamino)-acetamide | 0.07 (A), 0.20 (B) | 305 (M+H+, LC-MS) | 6.52 (N) |
| 218 | N-(4-Cyclohexyl-phenyl)-2-(3-morpholine-yl-propylamino)-acetamide | 0.07 (A), 0.08 (B) | 360 (M+H+, LC-MS) | 7.02 (N) |
| 219 | N-(4-Cyclohexyl-phenyl)-2-(2-pyrrolidin-1-yl-ethylamino)-acetamide | 0.07 (A) | 520 (LC-MS) | 7.03 (N) |
| 220 | 2-{[(4-Cyclohexyl-phenylcarbamoyl)-methyl]-amino}-pent-4-enoic acid | 0.26 (A), 0.41 (B) | 331 (M+H+, LC-MS) | 5.02 (N) |
| 221 | Acetic acid 2-[(4-cyclohexyl-phenylcarbamoyl)-methyl]-2-aza-bicyclo[2.2.1]hept-6-yl ester | 0.47 (A), 0.19 (B) | 371 (M+H+, LC-MS) | 3.87 (N) |
| 222 | 4-({[(4-Benzoyl-phenylcarbamoyl)-methyl] amino}-methyl)-benzoic acid | 0.21 (A), 0.67 (B) | 389 (M+H+, LC-MS) | 3.44 (N) |
| 223 | N-(4-Benzoyl-phenyl)-2-(1,1-dimethyl-prop-2-ynylamino)-acetamide | 0.53 (A), 0.50 (B) | 321 (M+H+, LC-MS) | 2.17 (N) |
| 224 | N-(4-Benzoyl-phenyl)-2-(cyclohexylmethyl-amino)-acetamide | 0.27 (A), 0.17 (B) | 351 (M+H+, LC-MS) | 6.03 (N) |
| 225 | {1-[(4-Benzoyl-phenylcarbamoyl)-methyl]-pyrrolidin-3-yl}-methyl-carbamic acid tert-butyl ester | 0.27 (A), 0.30 (B) | 438 (M+H+, LC-MS) | 3.84 (N) |
| 226 | N-(4-Benzoyl-phenyl)-2-(1-hydroxymethyl-butylamino)-acetamide | 0.10 (A), 0.47 (B) | 341 (M+H+, LC-MS) | 4.95 (N) |
| 227 | N-(4-Benzoyl-phenyl)-2-(4-hydroxy-butylamino)-acetamide | 0.05 (A), 0.30 (B) | 327 (M+H+, LC-MS) | 4.05 (N) |
| 228 | N-(4-Benzoyl-phenyl)-2-(3-morpholin-4-yl-propylamino)-acetamide | 0.05 (A), 0.17 (B) | 382 (M+H+, LC-MS) | 4.30 (N) |
| 229 | N-(4-Benzoyl-phenyl)-2-(2-pyrrolidin-1-yl-ethylamino)-acetamide | 0.63 (A), 0.05 (B) | 352 (M+H+, LC-MS) | 1.36 (N) |
| 230 | 2-{[(4-Benzoyl-phenylcarbamoyl)-methyl]-amino}-pent-4-enoic acid | 0.17 (A), 0.67 (B) | 353 (M+H+, LC-MS) | 3.43 (N) |

TABLE 1-continued

| Compound | NAME | TLC | MS | HPLC |
|---|---|---|---|---|
| 231 | Acetic acid 2-[(4-benzoyl-phenylcarbamoyl)-methyl]-2-aza-bicyclo[2.2.1]hept-6-yl ester | 0.41 (A), 0.38 (B) | 393 (M+H+, LC-MS) | 2.43 (N) |
| 233 | 4,4-Dicyano-3-{[(4-cyclohexyl-phenylcarbamoyl)-methyl]-amino}-but-3-enoic acid ethyl ester | 0.20 (A), 0.40 (B) | 387 (LC-MS) | 5.00 (N) |
| 234 | N-(4-Cyclohexyl-phenyl)-2-(3-imidazol-1-yl-propylamino)-acetamide | 0.05 (A), 0.15 (B) | 341 (M+H+, LC-MS) | 2.57 (N) |
| 235 | 2-Allylamino-N-(4-cyclohexyl-phenyl)-acetamide | 0.20 (A), 0.40 (B) | 341 (M+H+, LC-MS) | 7.32 (N) |
| 236 | N-(4-Cyclohexyl-phenyl)-2-(4-diethylamino-1-methyl-butylamino)-acetamide | 0.05 (A), 0.05 (B) | 374 (M+H+, LC-MS) | 2.8 1 (N) |
| 237 | 2-(2-Cyano-1-methyl-vinylamino)-N-(4-cyclohexyl-phenyl)-acetamide | 0.22 (A), 0.40 (B) | 374 (LC-MS) | 5.00 (N) |
| 238 | 3-{[(4-Cyclohexyl-phenylcarbamoyl)-methyl]-amino}-but-2-enoic acid methyl ester | 0.21 (A), 0.40 (B) | 374 (M+H+, LC-MS) | 5.00 (N) |
| 239 | 2-Cyclohexylamino-N-(-4-cyclohexyl-phenyl)-acetamide | 0.39 (A), 0.07 (B) | 315 (M+H+, LC-MS) | 4.13 (N) |
| 240 | N-(4-Cyclohexyl-phenyl)-2-[2-(2-hydroxy-ethoxy)-ethylamino]-acetamide | 0.10 (A), 0.28 (B) | 321 (M+H+, LC-MS) | 6.42 (N) |
| 241 | N-(4-Cyclohexyl-phenyl)-2-(2,2-dimethoxy-ethylamino)-acetamide | ND | ND | ND |
| 242 | N-(4-Benzoyl-phenyl)-2-cyclobutylamino-acetamide | 0.12 (A), 0.24 (B) | 309 (M+H+, LC-MS) | 2.05 (N) |
| 243 | 3-{[(4-Benzoyl-phenylcarbamoyl)-methyl]-amino}-4,4-dicyano-but-3-enoic acid ethyl ester | 0.20 (A), 0.63 (B) | 318 (LC-MS) | 3.43 (N) |
| 244 | N-(4-Benzoyl-phenyl)-2-(3-imidazol-1-yl-propylamino)-acetamide | 0.00 (A), 0.37 (B) | 363 (M+H+, LC-MS) | 1.18 (N) |
| 245 | 2-Allylamino-N-(4-benzoyl-phenyl)-acetamide | 0.17 (A), 0.13 (B) | 295 (M+H+, LC-MS) | 4.62 (N) |
| 246 | N-(4-Benzoyl-phenyl)-2-(4-diethylamino-1-methyl-butylamino)-acetamide | 0.05 (A), 0.05 (B) | 396 (M+H+, LC-MS) | 1.50 (N) |
| 247 | N-(4-Benzoyl-phenyl)-2-(2-cyano-1-methyl-vinylamino)-acetamide | 0.20 (A), 0.63 (B) | 320 (M+H+, LC-MS) | 3.43 (N) |
| 248 | 3-{[(4-Benzoyl-phenylcarbamoyl)-methyl]-amino}-but-2-enoic acid methyl ester | 0.20 (A), 0.63 (B) | 352 (M+H+, LC-MS) | 3.44 (N) |
| 249 | N-(4-Benzoyl-phenyl)-2-cyclohexylamino-acetamide | 0.17 (A), 0.20 (B) | 337 (M+H+, LC-MS) | 5.30 (N) |
| 250 | N-(4-Benzoyl-phenyl)-2-[2-(2-hydroxy-ethoxy)-ethylamino]-acetamide | 0.05 (A), 0.52 (B) | 343 (M+H+, LC-MS) | 1.47 (N) |

Example 3

This Example sets forth a second procedure that uses traditional techniques under the conditions described in Example 2 for synthesizing compounds of this invention.

Compound 251: N-(4-Cyclohexyl-phenyl)-2-[4-(2-oxo-2,3-dihydrobenzoimidazol-1-yl)-piperidin-1-yl]-acetamide

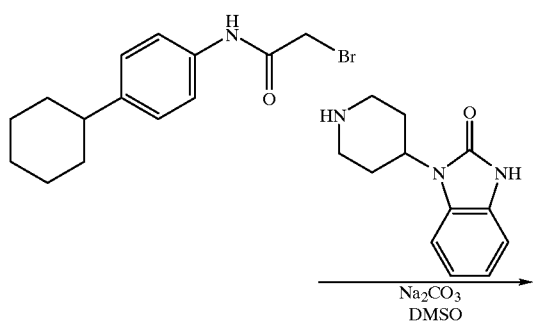

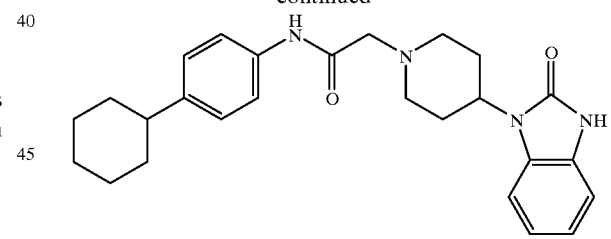

A mixture of N-(4-cyclohexyl-phenyl)-2-bromoacetamide (50 mg, 0.17 mmol), 4-(2-keto-1-benzimidazolinyl)-piperidine (41 mg, 0.18 mmol), and potassium carbonate (34 mg, 0.25 mmol) in dimethylsulfoxide (2 mL) was stirred at room temperature for 2 hours. The mixture was diluted with water and extracted with ethyl acetate (3×10 mL). The combined organic layer was washed with saturated aqueous sodium chloride solution, dried over $MgSO_4$, and concentrated to give a yellow oil. The crude oil was purified on reverse phase silica gel column using 100% acetonitrile to give N-(4-cyclohexyl-phenyl)-2-[4-(2-oxo-2,3-dihydrobenzoimidazol-1-yl)-piperidin-1-yl]-acetamide as a yellow solid (21 mg, 30%): mp 130–132° C. $^1$H NMR (300 MHz, $CDCl_3$) d 9.28 (s, 1 H), 9.05 (s, 1 H), 7.53 (d, 2 H), 7.22 (d, 2 H), 7.11 (m, 4 H), 4.33 (m, 1 H), 3.22 (s, 2 H), 3.12

(d, 2 H), 2.40–2.60 (m, 5 H), 1.70–1.90 (m, 7 H), 1.20–1.60 (m, 5 H). MS m/z 433 (M+H⁺).

Example 4

Compound 252: N-(4-Cyclohexyl-phenyl)-2-(piperidine)-acetamide

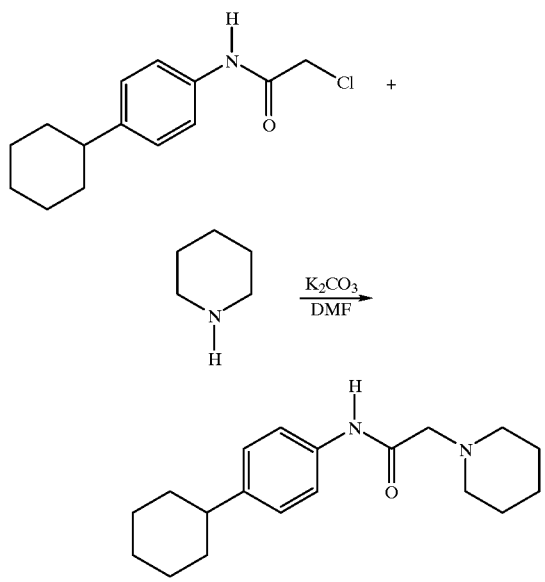

To 0.17 g of N-(4-cyclohexyl-phenyl)-2-chloroacetamide in 2.0 mL of DMF was added 0.11 g of $K_2CO_3$ and 0.1 mL of 1-piperidine. This mixture was stirred at rt for 2.5 hr. The reaction mixture was diluted with $H_2O$ and extracted with EtOAc. The organic layer was washed with brine, dried over $MgSO_4$, filtered and concentrated under reduced pressure. The product was redissolved in $CHCl_3$ and washed with $H_2O$ and brine. The organic layer was dried over $MgSO_4$, filtered and concentrated under reduced pressure to provided 0.129 g (62%) of the desired compound as a tan solid. mp=118–119° C.; ¹H NMR (300 MHz, $CDCl_3$) d 9.18 (br s, 1H), 7.48 (d, J=8.5 Hz, 2H), 7.17 (d, J=8.5 Hz, 2H), 3.05 (s, 2H) 2.54–2.40 (m, 5H), 1.86–1.20 (m, 16H); MS (EI) m/e: 301 (M+H).

The compounds of this invention that were prepared in analogy to the procedure of Example 4 are set forth in Table 2, below.

TABLE 2

| Compound | NAME | MP |
|---|---|---|
| 253 | 2-[4-(2-Oxo-2,3-dihydro-benzoimidazol-1-yl)-piperidin-1-yl]-N-(4-propyl-phenyl)-acetamide | 116–117 |
| 254 | N-(4-Butyl-phenyl)-2-[4-(2-oxo-2,3-dihydro-benzoimidazol-1-yl)-piperidin-1-yl]-acetamide | 130–131 |
| 255 | 2-[4-(2-Oxo-2,3-dihydro-benzoimidazol-1-yl)-piperidin-1-yl]-N-(4-pentyl-phenyl)-acetamide | 127–128 |
| 256 | N-(4-Hexyl-phenyl)-2-[4-(2-oxo-2,3-dihydro-benzoimidazol-1-yl)-piperidin-1-yl]-acetamide | 128–129 |
| 257 | N-(4-Isopropyl-phenyl)-2-[4-(2-oxo-2,3-dihydro-benzoimidazol-1-yl)-piperidin-1-yl]-acetamide | 133–134 |
| 258 | N-(4-Benzyl-phenyl)-2-[4-(2-oxo-2,3-dihydro-benzoimidazol-1-yl)-piperidin-1-yl]-acetamide | 182–3 |
| 259 | N-(4'-Fluoro-biphenyl-4-yl)-2-[4-(2-oxo-2,3-dihydro-benzoimidazol-1-yl)-piperidin-1-yl]-acetamide | 228–9 |

TABLE 2-continued

| Compound | NAME | MP |
|---|---|---|
| 260 | 4-{2-[4-(2-Oxo-2,3-dihydro-benzoimidazol-1-yl)-piperidin-1-yl]-acetylamino}-benzoic acid isopropyl ester | 166–7 |
| 261 | (4-{2-[4-(2-Oxo-2,3-dihydro-benzoimidazol-1-yl)-piperidin-1-yl]-acetylamino}-phenyl)-acetic acid ethyl ester | 164–5 |
| 262 | 2-[4-(2-Oxo-2,3-dihydro-benzoimidazol-1-yl)-piperidin-1-yl]-N-(4-styryl-phenyl)-acetamide | 234–5 |
| 263 | N-(4-Benzoyl-phenyl)-2-[4-(2-oxo-2,3-dihydro-benzoimidazol-1-yl)-piperidin-1-yl]-acetamide; hydrochloride | 215–6 |
| 264 | 4-{2-[4-(2-Oxo-2,3-dihydro-benzoimidazol-1-yl)-piperidin-1-yl]-acetylamino}-benzoic acid P-tolyl ester; hydrochloride | 197Z |
| 265 | 2-[4-(2-Oxo-2,3-dihydro-benzoimidazol-1-yl)-piperidin-1-yl]-N-[4-(oxo-phenyl-acetyl)-phenyl]-acetamide; hydrochloride | 185Z |
| 266 | 2-[4-(2-Oxo-2,3-dihydro-benzoimidazol-1-yl)-piperidin-1-yl]-N-(9-oxo-9H-fluoren-3-yl)-acetamide | 175–6 |
| 267 | N-(4-Oxazol-5-yl-phenyl)-2-[4-(2-oxo-2,3-dihydro-benzoimidazol-1-yl)-piperidin-1-yl]-acetamide; hydrate | 177–8 |
| 268 | N-(3-Benzoyl-phenyl)-2-[4-(2-oxo-2,3-dihydro-benzoimidazol-1-yl)-piperidin-1-yl]-acetamide | 134–5 |
| 269 | N-(4-Cyclohexyl-phenyl)-2-(4-oxo-1-phenyl-1,3,8-triaza-spiro[4.5]dec-8-yl)-acetamide | 117–118 |
| 270 | N-(4-Cyclohexyl-phenyl)-N-methyl-2-[4-(2-oxo-2,3-dihydro-benzoimidazol-1-yl)-piperidin-1-yl]-acetamide | 250–253 |
| 271 | N-Biphenyl-4-yl-2-piperidin-1-yl-acetamide | 102–103 |
| 272 | N-(4-Cyclohexyl-phenyl)-2-(4-phenyl-piperazin-1-yl)-acetamide | 195–196 |
| 273 | 2-(Benzhydryl-amino)-N-(4-cyclohexyl-phenyl)-acetamide | 132–133 |
| 274 | N-(4-Cyclohexyl-phenyl)-2-[4-(3-phenyl-ureido)-piperidin-1-yl]-acetamide | 222–223 |
| 275 | N-Biphenyl-4-yl-2-[4-(2-oxo-2,3-dihydro-benzoimidazol-1-yl)-piperidin-1-yl]-acetamide | 180–181 |
| 276 | N-(4-Cyclohexyl-phenyl)-2-[3-(2-oxo-2,3-dihydro-benzoimidazol-1-yl)-propylamino]-acetamide | |
| 277 | N-Biphenyl-4-yl-2-[3-(2-oxo-2,3-dihydro-benzoimidazol-1-yl)-propylamino]-acetamide | |
| 278 | N-(4-Cyclohexyl-phenyl)-2-[4-(2-oxo-2,3-dihydro-benzoimidazol-1-yl)-piperidin-1-yl]-propionamide | 148–150 |
| 279 | N-(4-#tert!-Butyl-phenyl)-2-[4-(2-oxo-2,3-dihydro-benzoimidazol-1-yl)-piperidin-1-yl]-propionamide | 144–148 |
| 280 | 2-[4-(2-Oxo-2,3-dihydro-benzoimidazol-1-yl)-piperidin-1-yl]-N-phenethyl-acetamide; hydrochloride | 181–2 |
| 281 | N-(2-Diisopropylamino-ethyl)-2-[4-(2-oxo-2,3-dihydro-benzoimidazol-1-yl)-piperidin-1-yl]-acetamide | 195–6 |
| 282 | N-Cyclohexylmethyl-2-[4-(2-oxo-2,3-dihydro-benzoimidazol-1-yl)-piperidin-1-yl]-acetamide; hydrochloride | 196–7 |
| 283 | N-(3-isopropoxy-propyl)-2-[4-(2-oxo-2,3-dihydro-benzoimidazol-1-yl)-piperidin-1-yl]-acetamide; hydrochloride | 237–8 |
| 284 | N-(2-Methoxy-ethyl)-2-[4-(2-oxo-2,3-dihydro-benzoimidazol-1-yl)-piperidin-1-yl]-acetamide | 77–8 |
| 285 | 2-[4-(2-Oxo-2,3-dihydro-benzoimidazol-1-yl)-piperidin-1-yl]-N-(tetrahydro-furan-2-ylmethyl)-acetamide | 179–80 |
| 288 | N-Cyclopentyl-2-[4-(2-oxo-2,3-dihydro-benzoimidazol-1-yl)-piperidin-1-yl]-acetamide; compound with oxalic acid | 217–8 |
| 289 | N-(3-isopropoxy-propyl)-2-[4-(2-oxo-2,3-dihydro-benzoimidazol-1-yl)-piperidin-1-yl]-acetamide | 67–8 |
| 290 | 2-(3-Acetylamino-pyrrolidin-1-yl)-N-(4-cyclohexyl-phenyl)-acetamide | 105–110 |
| 291 | 2-(Benzyl-ethyl-amino)-N-(4-cyclohexyl-phenyl)-acetamide | |

TABLE 2-continued

| Compound | NAME | MP |
|---|---|---|
| 292 | N-(4-Cyclohexyl-phenyl)-2-[4-(4-fluoro-benzoyl)-piperidin-1-yl]-acetamide; hydrochloride | 258 |
| 293 | 2-(3-Acetylamino-pyrrolidin-1-yl)-N-(4-cyclohexyl-phenyl)-acetamide; compound with oxalic acid | 122 |
| 294 | N-(4-Cyclohexyl-phenyl)-2-(4-phenyl-4-propoxy-piperidin-1-yl)-acetamide; hydrochloride | |
| 295 | 2-(4-Cyano-4-phenyl-piperidin-1-yl)-N-(4-cyclohexyl-phenyl)-acetamide; hydrochloride | |
| 296 | N-(4-Cyclohexyl-phenyl)-2-[2-(hydroxy-diphenyl-methyl)-pyrrolidin-1-yl]-acetamide; compound with oxalic acid | |
| 297 | 1-[(4-Cyclohexyl-phenylcarbamoyl)-methyl]-pyrrolidine-2-carboxylic acid amide; hydrochloride | |
| 298 | N-(4-Cyclohexyl-phenyl)-2-(4-hydroxy-4-p-tolyl-piperidin-1-yl)-acetamide; hydrochloride | |
| 299 | 2-[4-(2-Chloro-phenyl)-piperazin-1-yl]-N-(4-cyclohexy-phenyl-acetamide; compound with oxalic acid | |
| 300 | 2-[4-(Cyano-phenyl-methyl)-piperidin-1-yl]-N-(4-cyclohexyl-phenyl)-acetamide; hydrochloride | 150 |
| 301 | 2-[4-(Acetylamino-methyl)-4-phenyl-piperidin-1-yl]-N-(4-cyclohexyl-phenyl)-acetamide; compound with oxalic acid | 146 |
| 302 | 1-[(4-Cyclohexyl-phenylcarbamoyl)-methyl]-4-ethylamino-piperidine-4-carboxylic acid amide; compound with oxalic acid | 184 |
| 303 | N-(4-Cyclohexyl-phenyl)-2-(4-phenyl-4-propionyl-piperidin-1-yl)-acetamide; hydrochloride | 252 |
| 304 | 2-(3-Acetylamino-pyrrolidin-1-yl)-N-(4-benzoyl-phenyl)-acetamide; compound with oxalic acid | 100 |
| 305 | 1-[1-(2-Azocan-1-yl-2-oxo-ethyl)-piperidin-4-yl]-1,3-dihydro-benzoimidazol-2-one; hydrochloride | 158 |
| 306 | 2-[4-(2-Oxo-2,3-dihydro-benzoimidazol-1-yl)-piperidin-1-yl]-N-(9-oxo-9H-fluoren-2-yl)-acetamide; hydrochloride | 204 |
| 307 | 2-[4-(2-Oxo-2,3-dihydro-benzoimidazol-1-yl)-piperidin-1-yl]-N-(9-oxo-9H-fluoren-1-yl)-acetamide; hydrochloride | 204 |
| 308 | 2-[4-(2-Oxo-2,3-dihydro-benzoimidazol-1-yl)-piperidin-1-yl]-N-(9-oxo-9H-fluoren-4-yl)-acetamide | 205 |
| 309 | 1-[1-(2-Azepan-1-yl-2-oxo-ethyl)-piperidin-4-yl]-1,3-dihydro-benzoimidazol-2-one | 166 |
| 310 | N-Dibenzofuran-2-yl-2-[4-(2-oxo-2,3-dihydro-benzoimidazol-1-yl)-piperidin-1-yl]-acetamide; hydrochloride | 186 |
| 311 | 2-[4-(2-Oxo-2,3-dihydro-benzoimidazol-1-yl)-piperidin-1-yl]-N-(9-oxo-9H-fluoren-3-yl)-acetamide; hydrochloride | 258 |
| 312 | N-Biphenyl-4-yl-2-[4-(2-oxo-2,3-dihydro-benzoimidazol-1-yl)-piperidin-1-yl]-2-phenyl-acetamide | 207–210 |
| 313 | N-(4-Cyclohexyl-phenyl)-2-[4-(2-oxo-2,3-dihydro-benzoimidazol-1-yl)-piperidin-1-yl]-2-phenyl-acetamide | 217–210 |
| 314 | 2-(4-Benzyl-4-hydroxy-piperidin-1-yl)-N-(4-cyclohexyl-phenyl)-acetamide; hydrochloride | |
| 315 | 2-(4-Benzyl-4-hydroxy-piperidin-1-yl)-N-biphenyl-4-yl-acetamide; hydrochloride | |
| 316 | N-Biphenyl-4-yl-2-[2-(4-hydroxy-3-methoxy-phenyl)-ethylamino]-acetamide; hydrochloride | |
| 317 | N-Biphenyl-4-yl-2-(4-phenyl-4-propionyl-piperidin-1-yl)-acetamide; hydrochloride | |
| 319 | 2-[4-(2-Oxo-2,3-dihydro-benzoimidazol-1-yl)-piperidin-1-yl]-N-(4-phenylamino-phenyl)-acetamide; hydrochloride | |
| 322 | N-Benzhydryl-2-[4-(2-oxo-2,3-dihydro-benzo-imidazol-1-yl)-piperidin-1-yl]-acetamide; hydrochloride | |
| 323 | N-Biphenyl-3-yl-2-[4-(2-oxo-2,3-dihydro-benzo-imidazol-1-yl)-piperidin-1-yl]-acetamide; hydrochloride | |
| 324 | N-Biphenyl-2-yl-2-[4-(2-oxo-2,3-dihydro-benzo-imidazol-1-yl)-piperidin-1-yl]-acetamide; hydrochloride | |
| 325 | N-(9H-Fluoren-2-yl)-2-[4-(2-oxo-2,3-dihydro-benzoimidazol-1-yl)-piperidin-1-yl]-acetamide | |
| 326 | N-Bicyclo[2.2.1]hept-2-yl-2-[4-(2-oxo-2,3-dihydro-benzoimidazol-1-yl)-piperidin-1-yl]-acetamide | |
| 327 | N-(4'-Fluoro-biphenyl-4-yl)-2-[4-(2-oxo-2,3-dihydro-benzoimidazol-1-yl)-piperidin-1-yl]-acetamide; hydrochloride | 289 |
| 328 | N-(4-Methoxy-biphenyl-3-yl)-2-[4-(2-oxo-2,3-dihydro-benzoimidazol-1-yl)-piperidin-1-yl]-acetamide; hydrochloride | |
| 329 | N-Biphenyl-4-yl-2-[4-(2-oxo-2,3-dihydro-benzo-imidazol-1-yl)-piperidin-1-yl]-propionamide; hydrochloride | |

Example 5

The compounds prepared in Examples 2–4 as well as the prior art compounds set forth in Table 4, below, were tested for NPY Y5 receptor binding affinity according to one or more of the protocols set forth below.

A. Human NPY1 Receptor Binding Assay

This is a modification of Gordon et al., (J. Neurochem. 55:506–513, 1990). SK-N-MC cells (ATCC, Rockville, Md.) were plated in 24-well plates. Once confluent, cells were rinsed with Dulbecco's phosphate buffered saline (DPBS). Cells were then preincubated in binding buffer containing serum-free DMEM, 25 mM HEPES (pH 7.3), 0.5% bovine serum albumin (BSA), 0.1% bacitracin and 0.1 mM phenylmethylsulfonylfluoride for 30 minutes at room temperature. Drug dilution and [125I]PYY (~50 pM: NEN-DuPont) were added to the wells, and the cells were incubated for an additional 3 hours at room temperature, followed by rinsing with ice-cold DPBS. Nonspecific binding was defined with 1 $\mu$M NPY. After lysing the cells with 1% Triton X-100, the amount of radioactivity in the lysates was quantitated with a gamma counter. IC50 values, which correspond to 50% inhibition of specific binding, were determined with non-linear regression analysis. The results of compounds tested according to this protocol are reported in Table 3.

B. Human Y2 and Y4/PP1 Receptor Binding Assays

Binding assays were performed on GF/C Millipore 96-well plates pretreated with 0.02% polyethylenimine. The binding buffer for rat Y2 binding is Krebs-Ringer bicarbonate (pH 7.4) containing 0.01% BSA and 0.005% bacitracin. Samples consist of membrane protein, 25 pM [125I]PYY and drug dilution. Nonspecific binding is defined by 1 $\mu$M NPY. The binding buffer for human Y4/PP1 binding consists of 137 mM NaCl, 5.4 mM KCl, 0.44 mM KH2PO4, 1.26 mM CaCl2, 0.81 mM MgSO4, 20 mM HEPES, 1 mM dithiothreitol, 0.1% bacitracin, 100 mg/l streptomycin sulfate, 1 mg/l aprotinin, 10 mg/ml soybean trypsin inhibitor and 0.3% BSA, pH 7.4. Samples consist of membrane protein, 50 pM human [125I]human PP (hPP: NEN DuPont, Boston, Mass.) and drug dilution. 1 $\mu$M hPP is used to define nonspecific binding.

After a 2 hour incubation at room temperature with constant mixing, the samples are aspirated on a vacuum manifold, and rinsed with ice-cold binding buffer. The amount of radioactivity in each well is quantitated with either gamma counting or liquid scintillation. IC50 values, which correspond to 50% inhibition of specific binding, are determined with non-linear regression analysis. The results of compounds tested according to this protocol are reported in Table 3.

C. Human and Rat NPY5 Receptor Binding Assays

Binding assays are performed on GF/C Millipore 96-well plates pretreated with 0.02% polyethylenimine. The binding buffer is 25 mM Tris, 120 mM NaCl, 5 mM KCl, 1.2 mM KH2PO4, 2.5 mM CaCl2, 1.2 mM MgSO4, 0.1% BSA and 0.5 mg/ml bacitracin, pH 7.4. Samples consist of membrane protein, 75–100 pM [125I]PYY (porcine, NEN-DuPont) and drug dilution. Nonspecific binding is defined by 1 $\mu$M PYY. After a 2 hour incubation at room temperature with constant mixing, the samples are aspirated on a vacuum manifold, and rinsed with ice-cold binding buffer. The amount of radioactivity in each well is quantitated with either gamma counting or liquid scintillation. IC50 values, which correspond to 50% inhibition of specific binding, are determined with non-linear regression analysis. The results of compounds tested according to this protocol are reported in Table 3.

D. Rat NYP5 Cyclase Assay (In Vitro Functional Assay)

Cells stably expressing the rat NPY5 receptor are resuspended in serum-free DMEM containing 10 mM HEPES (pH 7.4) and 1 mM isobutylmethylxanthine (IBMX). 1 mM forskolin and drug dilution are then added to the cells. After a 20 minute incubation of the samples at 37° C., the assay is stopped by placing the samples in boiling water for 3 minutes. The cAMP produced in each sample is quantitated with a radioimmunoassay kit (NEN DuPont). Data are expressed as a percentage of forskolin-stimulated adenylate cyclase. The results of compounds tested according to this protocol are reported in Table 3.

TABLE 3

| Compound | hNPY1 IC50 ($\mu$M) | hNPY2 IC50 ($\mu$M) | hNPY4 IC50 ($\mu$M) | hNPY5 IC50 ($\mu$M) | rNPY5 IC50 ($\mu$M) | rNPY5 % FSAC (10 $\mu$M) |
|---|---|---|---|---|---|---|
| 1 | ND | >5 | ND | 0.15 | ND | ND |
| 2 | ND | >5 | ND | 0.78 | ND | ND |
| 3 | ND | >5 | ND | 0.19 | ND | ND |
| 4 | ND | >5 | ND | 0.53 | ND | ND |
| 5 | ND | ND | ND | 0.3 | 0.3 | ND |
| 6 | ND | >5 | ND | 0.8 | ND | ND |
| 7 | ND | >5 | ND | 1.6 | ND | ND |
| 8 | ND | >5 | ND | 0.96 | ND | ND |
| 9 | ND | >5 | ND | 0.64 | ND | ND |
| 10 | ND | >5 | ND | 2.9 | ND | ND |
| 11 | ND | >5 | ND | 2.8 | ND | ND |
| 12 | ND | >5 | ND | 8.9 | ND | ND |
| 13 | ND | >5 | ND | 9.1 | ND | ND |
| 14 | ND | >5 | ND | 1.8 | ND | ND |
| 15 | ND | >5 | ND | 2.7 | ND | ND |
| 16 | ND | >5 | ND | 9.6 | ND | ND |
| 17 | ND | >5 | ND | 1.2 | ND | ND |
| 18 | ND | >5 | ND | 5.2 | ND | ND |
| 19 | ND | >5 | ND | 0.4 | ND | ND |
| 20 | ND | >5 | ND | 7.8 | ND | ND |
| 21 | ND | >5 | ND | 0.63 | ND | ND |
| 22 | ND | >5 | ND | 9.9 | ND | ND |
| 23 | ND | >5 | ND | >10 | ND | ND |
| 24 | ND | >5 | ND | 2.9 | ND | ND |
| 25 | ND | >5 | ND | 1.9 | ND | ND |
| 26 | ND | >5 | ND | 0.093 | 0.037 | 111 |
| 27 | ND | >5 | ND | 1.7 | ND | ND |
| 28 | ND | >5 | ND | 8.9 | ND | ND |
| 29 | ND | >5 | ND | 4.4 | ND | ND |
| 30 | ND | >5 | ND | 0.06 | 0.013 | 107 |
| 31 | ND | >5 | ND | 1.2 | ND | ND |
| 32 | ND | >5 | ND | 3 | ND | ND |
| 33 | ND | >5 | ND | >10 | ND | ND |
| 34 | ND | >5 | ND | 1.4 | ND | ND |
| 35 | ND | >5 | ND | 0.63 | ND | ND |
| 36 | ND | >5 | ND | 0.71 | ND | ND |
| 37 | ND | >5 | ND | >10 | ND | ND |
| 38 | ND | >5 | ND | 8.5 | ND | ND |
| 39 | ND | >5 | ND | 2.1 | ND | ND |
| 40 | ND | >5 | ND | >10 | ND | ND |
| 41 | ND | >5 | ND | 0.06 | ND | ND |
| 42 | ND | >5 | ND | 1.6 | ND | ND |
| 43 | ND | >5 | ND | >10 | ND | ND |
| 44 | ND | >5 | ND | 0.093 | ND | ND |
| 45 | ND | >5 | ND | 8.5 | ND | ND |
| 46 | ND | >5 | ND | 0.005 | ND | ND |
| 47 | ND | >5 | ND | 1.2 | ND | ND |
| 48 | ND | >5 | ND | 0.02 | ND | ND |
| 49 | ND | >5 | ND | 8.8 | ND | ND |
| 50 | ND | >5 | ND | 2.2 | ND | ND |
| 51 | ND | >5 | ND | 3.3 | ND | ND |
| 52 | ND | >5 | ND | 0.029 | ND | ND |
| 53 | ND | >5 | ND | 0.44 | ND | ND |
| 54 | ND | >5 | ND | 7.3 | ND | ND |
| 55 | ND | >5 | ND | >10 | ND | ND |

TABLE 3-continued

| Compound | hNPY1 IC50 (µM) | hNPY2 IC50 (µM) | hNPY4 IC50 (µM) | hNPY5 IC50 (µM) | rNPY5 IC50 (µM) | rNPY5 % FSAC (10 µM) |
|---|---|---|---|---|---|---|
| 56 | ND | >5 | ND | 0.208 | ND | ND |
| 57 | ND | >5 | ND | 0.005 | ND | ND |
| 58 | ND | >5 | ND | 2 | ND | ND |
| 59 | ND | >5 | ND | 0.65 | ND | ND |
| 60 | ND | >5 | ND | 4.2 | ND | ND |
| 61 | ND | >5 | ND | 9.5 | ND | ND |
| 62 | ND | >5 | ND | 0.42 | ND | ND |
| 63 | ND | >5 | ND | 0.57 | ND | ND |
| 64 | ND | >5 | ND | 4.8 | ND | ND |
| 65 | ND | >5 | ND | 0.69 | ND | ND |
| 66 | ND | >5 | ND | 0.78 | ND | ND |
| 67 | ND | >5 | ND | 10 | ND | ND |
| 68 | ND | >5 | ND | 9.7 | ND | ND |
| 69 | ND | >5 | ND | 0.003 | ND | ND |
| 70 | ND | >5 | ND | 3.7 | ND | ND |
| 71 | ND | >5 | ND | 0.22 | ND | ND |
| 72 | ND | >5 | ND | 1 | ND | ND |
| 73 | ND | >5 | ND | >5 | ND | ND |
| 74 | ND | >5 | ND | 0.4 | ND | ND |
| 75 | ND | >5 | ND | 0.009 | ND | ND |
| 76 | ND | >5 | ND | 0.32 | ND | ND |
| 77 | ND | >5 | ND | 2.6 | ND | ND |
| 78 | ND | >5 | ND | >5 | ND | ND |
| 79 | ND | >5 | ND | 3.5 | ND | ND |
| 80 | ND | >5 | ND | 1.4 | ND | ND |
| 81 | ND | >5 | ND | >5 | ND | ND |
| 82 | ND | >5 | ND | >5 | ND | ND |
| 83 | ND | >5 | ND | 0.92 | ND | ND |
| 84 | ND | >5 | ND | 0.93 | ND | ND |
| 85 | ND | >5 | ND | 2.8 | ND | ND |
| 86 | ND | >5 | ND | 0.001 | ND | ND |
| 87 | ND | >5 | ND | 0.004 | ND | ND |
| 88 | ND | >5 | ND | 0.12 | ND | ND |
| 89 | ND | >5 | ND | 0.52 | ND | ND |
| 90 | ND | >5 | ND | 3.8 | ND | ND |
| 91 | ND | >5 | ND | 0.43 | ND | ND |
| 92 | ND | >5 | ND | 1.3 | ND | ND |
| 93 | ND | >5 | ND | 0.48 | ND | ND |
| 94 | ND | >5 | ND | 3.2 | ND | ND |
| 95 | ND | >5 | ND | 1.6 | ND | ND |
| 96 | ND | >5 | ND | 1.2 | ND | ND |
| 97 | ND | >5 | ND | 0.15 | ND | ND |
| 98 | ND | >5 | ND | >10 | ND | ND |
| 99 | ND | >5 | ND | 8.4 | ND | ND |
| 100 | ND | >5 | ND | 2.4 | ND | ND |
| 101 | ND | >5 | ND | 6.1 | ND | ND |
| 102 | ND | >5 | ND | 0.38 | ND | ND |
| 103 | ND | >5 | ND | 3 | ND | ND |
| 104 | ND | >5 | ND | 0.49 | ND | ND |
| 105 | ND | >5 | ND | 5.1 | ND | ND |
| 106 | ND | >5 | ND | 3 | ND | ND |
| 107 | ND | >5 | ND | 2.9 | ND | ND |
| 108 | ND | >5 | ND | 0.97 | ND | ND |
| 109 | ND | >5 | ND | >10 | ND | ND |
| 110 | ND | >5 | ND | 8.7 | ND | ND |
| 111 | ND | >5 | ND | 0.16 | ND | ND |
| 112 | ND | >5 | ND | 3.9 | ND | ND |
| 113 | ND | >5 | ND | 0.7 | ND | ND |
| 114 | ND | >5 | ND | 2.4 | ND | ND |
| 115 | ND | >5 | ND | >10 | ND | ND |
| 116 | ND | >5 | ND | 9.5 | ND | ND |
| 117 | ND | >5 | ND | 3 | ND | ND |
| 118 | ND | >5 | ND | 2 | ND | ND |
| 119 | ND | >5 | ND | 3.6 | ND | ND |
| 120 | ND | >5 | ND | >10 | ND | ND |
| 121 | ND | >5 | ND | 0.095 | ND | ND |
| 122 | ND | >5 | ND | 9.9 | ND | ND |
| 123 | ND | >5 | ND | 0.91 | ND | ND |
| 124 | ND | >5 | ND | 10 | ND | ND |
| 125 | ND | >5 | ND | 0.43 | ND | ND |
| 126 | ND | ND | ND | ND | ND | ND |
| 127 | ND | ND | ND | >5 | ND | ND |
| 128 | ND | ND | ND | ND | ND | ND |
| 129 | ND | ND | ND | ND | ND | ND |
| 130 | ND | ND | ND | ND | ND | ND |

TABLE 3-continued

| Compound | hNPY1 IC50 ($\mu$M) | hNPY2 IC50 ($\mu$M) | hNPY4 IC50 ($\mu$M) | hNPY5 IC50 ($\mu$M) | rNPY5 IC50 ($\mu$M) | rNPY5 % FSAC (10 $\mu$M) |
|---|---|---|---|---|---|---|
| 131 | ND | ND | ND | >5 | ND | ND |
| 132 | ND | ND | ND | ND | ND | ND |
| 133 | ND | ND | ND | ND | ND | ND |
| 134 | ND | ND | ND | >5 | ND | ND |
| 135 | ND | ND | ND | ND | ND | ND |
| 136 | ND | ND | ND | >5 | ND | ND |
| 137 | ND | ND | ND | >5 | ND | ND |
| 138 | ND | ND | ND | >5 | ND | ND |
| 139 | ND | ND | ND | >5 | ND | ND |
| 140 | ND | ND | ND | >5 | ND | ND |
| 141 | ND | ND | ND | >5 | ND | ND |
| 142 | ND | ND | ND | >5 | ND | ND |
| 143 | ND | ND | ND | >5 | ND | ND |
| 144 | ND | ND | ND | >5 | ND | ND |
| 145 | ND | ND | ND | >5 | ND | ND |
| 146 | ND | ND | ND | >5 | ND | ND |
| 147 | ND | ND | ND | >5 | ND | ND |
| 148 | ND | ND | ND | ND | ND | ND |
| 149 | ND | ND | ND | >5 | ND | ND |
| 150 | ND | ND | ND | >5 | ND | ND |
| 151 | ND | ND | ND | >5 | ND | ND |
| 152 | ND | ND | ND | >5 | ND | ND |
| 153 | ND | ND | ND | >5 | ND | ND |
| 154 | ND | ND | ND | >5 | ND | ND |
| 155 | ND | ND | ND | >5 | ND | ND |
| 156 | ND | ND | ND | >5 | ND | ND |
| 157 | ND | ND | ND | >5 | ND | ND |
| 158 | ND | ND | ND | >5 | ND | ND |
| 159 | ND | ND | ND | >5 | ND | ND |
| 160 | ND | ND | ND | 0.66 | 0.45 | ND |
| 161 | ND | ND | ND | ND | ND | ND |
| 162 | ND | ND | ND | ND | ND | ND |
| 163 | ND | ND | ND | ND | ND | ND |
| 164 | ND | ND | ND | ND | ND | ND |
| 165 | ND | ND | ND | 1.1 | 0.7 | ND |
| 166 | ND | ND | ND | 0.61 | 0.73 | ND |
| 167 | ND | ND | ND | ND | ND | ND |
| 168 | ND | ND | ND | ND | ND | ND |
| 169 | ND | ND | ND | ND | ND | ND |
| 170 | ND | ND | ND | ND | ND | ND |
| 171 | ND | ND | ND | 0.53 | 1.2 | ND |
| 172 | ND | ND | ND | ND | ND | ND |
| 173 | ND | ND | ND | 2 | 0.92 | ND |
| 174 | ND | ND | ND | 0.61 | 0.84 | ND |
| 175 | ND | ND | ND | ND | ND | ND |
| 176 | ND | ND | ND | >10 | >10 | ND |
| 177 | ND | ND | ND | ND | ND | ND |
| 178 | ND | ND | ND | ND | ND | ND |
| 179 | ND | ND | ND | >10 | >10 | ND |
| 180 | ND | ND | ND | 0.17 | 0.12 | ND |
| 181 | ND | ND | ND | 1 | 0.57 | ND |
| 182 | ND | ND | ND | ND | ND | ND |
| 183 | ND | ND | ND | ND | ND | ND |
| 184 | ND | ND | ND | 0.74 | 0.69 | ND |
| 185 | ND | ND | ND | ND | ND | ND |
| 186 | ND | ND | ND | ND | ND | ND |
| 187 | ND | ND | ND | ND | ND | ND |
| 188 | ND | ND | ND | ND | ND | ND |
| 189 | ND | ND | ND | ND | ND | ND |
| 190 | ND | ND | ND | 0.34 | 0.34 | ND |
| 191 | ND | ND | ND | ND | ND | ND |
| 192 | ND | ND | ND | ND | ND | ND |
| 193 | ND | ND | ND | 0.27 | 0.25 | ND |
| 194 | ND | ND | ND | 0.037 | 0.035 | ND |
| 195 | ND | ND | ND | 0.026 | 0.026 | ND |
| 196 | ND | ND | ND | 0.043 | 0.049 | ND |
| 197 | ND | ND | ND | 0.021 | 0.02 | ND |
| 198 | ND | ND | ND | 1 | 1.3 | ND |
| 199 | ND | ND | ND | 0.82 | 2.4 | ND |
| 200 | ND | ND | ND | 0.53 | 0.34 | ND |
| 201 | ND | ND | ND | ND | ND | ND |
| 202 | ND | ND | ND | 0.058 | 0.053 | ND |
| 203 | ND | ND | ND | 0.2 | 0.18 | ND |
| 204 | ND | ND | ND | ND | ND | ND |
| 205 | ND | ND | ND | 0.072 | 0.071 | ND |

TABLE 3-continued

| Compound | hNPY1 IC50 (μM) | hNPY2 IC50 (μM) | hNPY4 IC50 (μM) | hNPY5 IC50 (μM) | rNPY5 IC50 (μM) | rNPY5 % FSAC (10 μM) |
|---|---|---|---|---|---|---|
| 206 | ND | ND | ND | 0.042 | 0.048 | ND |
| 207 | ND | ND | ND | 0.048 | 0.05 | ND |
| 208 | ND | ND | ND | ND | ND | ND |
| 209 | ND | ND | ND | ND | ND | ND |
| 210 | ND | ND | ND | ND | ND | ND |
| 211 | ND | ND | ND | 1.3 | 1 | ND |
| 212 | ND | ND | ND | >10 | >10 | ND |
| 213 | ND | ND | ND | 0.36 | 0.36 | ND |
| 214 | ND | ND | ND | ND | ND | ND |
| 215 | ND | ND | ND | 0.17 | 0.3 | ND |
| 216 | ND | ND | ND | 0.45 | >10 | ND |
| 217 | ND | ND | ND | ND | ND | ND |
| 218 | ND | ND | ND | ND | ND | ND |
| 219 | ND | ND | ND | ND | ND | ND |
| 220 | ND | ND | ND | 0.54 | 0.72 | ND |
| 221 | ND | ND | ND | 0.029 | 0.029 | ND |
| 222 | ND | ND | ND | >10 | >10 | ND |
| 223 | ND | ND | ND | 0.54 | 1.4 | ND |
| 224 | ND | ND | ND | ND | ND | ND |
| 225 | ND | ND | ND | 0.32 | 0.19 | ND |
| 226 | ND | ND | ND | ND | ND | ND |
| 227 | ND | ND | ND | ND | ND | ND |
| 228 | ND | ND | ND | ND | ND | ND |
| 229 | ND | ND | ND | ND | ND | ND |
| 230 | ND | ND | ND | 0.81 | 2.5 | ND |
| 231 | ND | ND | ND | 0.067 | 0.074 | ND |
| 232 | ND | ND | ND | ND | ND | ND |
| 233 | ND | ND | ND | 0.53 | 0.88 | ND |
| 234 | ND | ND | ND | 0.95 | 0.61 | ND |
| 235 | ND | ND | ND | 1.6 | 3.8 | ND |
| 236 | ND | ND | ND | ND | ND | ND |
| 237 | ND | ND | ND | 4.4 | 1 | ND |
| 238 | ND | ND | ND | 0.65 | 0.55 | ND |
| 239 | ND | ND | ND | ND | ND | ND |
| 240 | ND | ND | ND | ND | ND | ND |
| 241 | ND | ND | ND | 0.28 | 0.23 | ND |
| 242 | ND | ND | ND | 4.4 | 5 | ND |
| 243 | ND | ND | ND | ND | ND | ND |
| 244 | ND | ND | ND | 0.67 | 3 | ND |
| 245 | ND | ND | ND | ND | ND | ND |
| 246 | ND | ND | ND | ND | ND | ND |
| 247 | ND | ND | ND | ND | ND | ND |
| 248 | ND | ND | ND | 1.6 | 1.7 | ND |
| 249 | ND | ND | ND | ND | ND | ND |
| 250 | ND | ND | ND | ND | ND | ND |
| 251 | >5 | >5 | >5 | 0.004 | ND | 92 |
| 252 | >5 | >5 | >5 | 0.94 | 0.63 | ND |
| 253 | >5 | >5 | >5 | 0.063 | 0.05 | 99 |
| 254 | >5 | >5 | >5 | 0.043 | ND | 103 |
| 255 | >5 | >5 | >5 | 0.074 | ND | 95 |
| 256 | >5 | >5 | >5 | 0.12 | ND | 92 |
| 257 | >5 | >5 | >5 | 0.11 | ND | 88 |
| 258 | >5 | >5 | >5 | 0.1 | ND | ND |
| 259 | >5 | >5 | >5 | 0.15 | 0.087 | 101 |
| 260 | >5 | >5 | >5 | 0.014 | ND | ND |
| 261 | >5 | >5 | >5 | 0.59 | ND | ND |
| 262 | >5 | >5 | >5 | 0.79 | ND | ND |
| 263 | ND | >5 | >5 | 0.004 | 0.003 | 97 |
| 264 | ND | >5 | >5 | 0.18 | 0.1 | 139 |
| 265 | >5 | >5 | >5 | 0.005 | 0.005 | 90 |
| 266 | >5 | >5 | >5 | 0.0005 | 0.0004 | ND |
| 267 | >5 | >5 | >5 | 0.15 | 0.15 | ND |
| 268 | >5 | >5 | >5 | 0.13 | 0.12 | ND |
| 269 | >5 | >5 | >5 | 0.79 | ND | ND |
| 270 | >5 | >5 | >5 | >10 | >10 | ND |
| 271 | >5 | >5 | >5 | 5.4 | 2.9 | ND |
| 272 | >5 | >5 | >5 | 0.117 | 0.21 | ND |
| 273 | >5 | ND | >5 | 7 | 6.5 | ND |
| 274 | >5 | ND | >5 | 4.8 | 1.5 | ND |
| 275 | >5 | >5 | >5 | 0.042 | 0.019 | 103 |
| 276 | ND | >5 | >5 | 1.1 | ND | ND |
| 277 | >5 | >5 | >5 | 0.89 | 1.6 | ND |
| 278 | >5 | >5 | >5 | 0.028 | 0.012 | ND |
| 279 | >5 | >5 | >5 | 0.13 | 0.068 | ND |
| 280 | >5 | >5 | >5 | ND | ND | 90 |

TABLE 3-continued

| Compound | hNPY1 IC50 (μM) | hNPY2 IC50 (μM) | hNPY4 IC50 (μM) | hNPY5 IC50 (μM) | rNPY5 IC50 (μM) | rNPY5 % FSAC (10 μM) |
|---|---|---|---|---|---|---|
| 281 | >5 | >5 | >5 | >10 | >10 | ND |
| 282 | >5 | >5 | >5 | 0.38 | 0.313 | ND |
| 283 | >5 | >5 | >5 | >10 | >10 | ND |
| 284 | >5 | >5 | >5 | >10 | >10 | ND |
| 285 | ND | >5 | >5 | ND | ND | ND |
| 286 | ND | >5 | >5 | ND | ND | ND |
| 287 | ND | >5 | >5 | ND | ND | ND |
| 288 | ND | >5 | >5 | ND | ND | ND |
| 289 | ND | >5 | >5 | ND | ND | ND |
| 290 | >5 | >5 | >5 | 0.038 | 0.019 | 101 |
| 291 | ND | ND | ND | ND | ND | ND |
| 292 | >5 | >5 | >5 | 0.11 | 0.084 | ND |
| 293 | >5 | >5 | >5 | 0.19 | 0.17 | ND |
| 294 | >5 | >5 | >5 | 0.051 | 0.05 | 101 |
| 295 | >5 | >5 | >5 | 0.0047 | 0.0045 | 101 |
| 296 | >5 | >5 | >5 | 0.048 | 0.043 | 98 |
| 297 | >5 | >5 | >5 | 0.032 | 0.045 | 103 |
| 298 | >5 | >5 | >5 | 0.03 | 0.044 | 103 |
| 299 | >5 | >5 | >5 | 0.14 | 0.16 | 103 |
| 300 | >5 | >5 | >5 | 0.013 | 0.013 | 90 |
| 301 | >5 | >5 | >5 | 0.032 | 0.032 | 101 |
| 302 | >5 | >5 | >5 | 0.006 | 0.006 | 107 |
| 303 | >5 | >5 | >5 | 0.004 | 0.006 | 93 |
| 304 | >5 | >5 | >5 | 0.15 | 0.18 | 85 |
| 305 | ND | >5 | >5 | ND | ND | ND |
| 306 | >5 | >5 | >5 | 0.044 | 0.035 | ND |
| 307 | ND | >5 | >5 | ND | ND | ND |
| 308 | >5 | >5 | >5 | 0.36 | 0.3 | ND |
| 309 | ND | >5 | >5 | ND | ND | ND |
| 310 | >5 | >5 | >5 | 0.034 | 0.034 | ND |
| 311 | >5 | >5 | >5 | 0.00047 | 0.00034 | 95 |
| 312 | >5 | >5 | >5 | 0.032 | 0.024 | ND |
| 313 | >5 | >5 | >5 | 0.035 | 0.02 | ND |
| 314 | >5 | >5 | >5 | 0.13 | 0.1 | 110 |
| 315 | ND | ND | ND | 0.8 | 2 | ND |
| 316 | ND | ND | ND | ND | ND | ND |
| 317 | ND | ND | ND | 0.01 | 0.011 | ND |
| 318 | ND | ND | ND | ND | ND | ND |
| 319 | ND | ND | ND | ND | ND | ND |
| 320 | ND | ND | ND | ND | ND | ND |
| 321 | ND | ND | ND | ND | ND | ND |
| 322 | ND | >5 | ND | ND | ND | ND |
| 323 | >5 | ND | >5 | 0.026 | 0.026 | ND |
| 324 | >5 | >5 | >5 | 0.39 | 0.69 | ND |
| 325 | >5 | >5 | >5 | 0.006 | 0.004 | ND |
| 326 | ND | >5 | >5 | ND | ND | ND |
| 327 | >5 | >5 | >5 | 0.11 | 0.06 | 101 |
| 328 | ND | >5 | >5 | ND | ND | ND |
| 329 | >5 | >5 | >5 | 0.02 | 0.016 | ND |
| 330 | >5 | >5 | >5 | 0.44 | 0.26 | 99 |
| 331 | ND | >5 | >5 | ND | ND | ND |
| 332 | >5 | >5 | >5 | 0.61 | 0.53 | ND |
| 333 | ND | >5 | >5 | ND | ND | ND |
| 334 | ND | >5 | >5 | ND | ND | ND |
| 335 | >5 | >5 | >5 | 0.11 | 0.098 | ND |
| 336 | >5 | >5 | >5 | 0.22 | 0.205 | ND |
| 337 | >5 | ND | >5 | 0.096 | 0.108 | ND |
| 338 | >5 | >5 | >5 | 0.91 | 1.2 | ND |
| 339 | >5 | >5 | >5 | 0.034 | 0.031 | ND |
| 340 | >5 | >5 | >5 | 0.227 | 0.25 | ND |
| 341 | >5 | >5 | >5 | 0.33 | 0.29 | ND |
| 342 | >5 | >5 | >5 | 0.276 | 0.37 | 105 |
| 343 | >5 | >5 | >5 | 0.11 | 0.045 | ND |
| 344 | >5 | >5 | >5 | 2.7 | 1.7 | ND |
| 345 | >5 | >5 | >5 | 2.9 | 3.3 | 93 |
| 346 | >5 | >5 | >5 | 0.081 | 0.063 | 105 |
| 347 | >5 | >5 | >5 | 0.143 | 0.13 | ND |
| 348 | >5 | >5 | >5 | 1.2 | >10 | ND |
| 349 | >5 | >5 | >5 | 0.138 | 0.165 | 100 |
| 350 | >5 | >5 | >5 | 2.3 | 1.4 | ND |
| 351 | >5 | >5 | >5 | 0.58 | 0.979 | ND |
| 352 | >5 | >5 | >5 | 0.053 | 0.0628 | 90 |
| 353 | >5 | >5 | >5 | 0.135 | 0.187 | ND |
| 354 | >5 | >5 | >5 | 0.143 | 0.136 | 98 |
| 355 | >5 | >5 | >5 | 0.2 | 0.19 | ND |

TABLE 3-continued

| Compound | hNPY1 IC50 (μM) | hNPY2 IC50 (μM) | hNPY4 IC50 (μM) | hNPY5 IC50 (μM) | rNPY5 IC50 (μM) | rNPY5 % FSAC (10 μM) |
|---|---|---|---|---|---|---|
| 356 | >5 | >5 | >5 | 0.259 | 0.271 | 105 |
| 357 | >5 | >5 | >5 | 0.239 | 0.229 | 112 |
| 358 | >5 | >5 | >5 | 0.73 | 0.443 | ND |
| 359 | >5 | >5 | >5 | 1.3 | 1.2 | 104 |
| 360 | >5 | >5 | >5 | 0.055 | 0.0562 | ND |
| 361 | >5 | >5 | >5 | 0.41 | 0.539 | ND |
| 362 | >5 | ND | >5 | 0.2 | 0.115 | ND |

Compounds 330–362, each tested according to one or more assays set forth in this Example are known compounds. The name of each known compound and it source is set fourth Table 4 immediately below.

TABLE 4

| Compound | NAME | Reference |
|---|---|---|
| 330 | N-(2,6-Dibromo-4-ethyl-phenyl)-2-[4-(2-oxo-2,3-dihydro-benzoimidazol-1-yl)-piperidin-1-yl]-acetamide | EP-628555-A1 |
| 331 | N-(2-Amino-phenyl)-2-[4-(2-oxo-2,3-dihydro-benzoimidazol-1-yl)-piperidin-1-yl]-acetamide | EP-628555-A1 |
| 332 | N-(2,4-Difluoro-benzyl)-2-[4-(2-oxo-2,3-dihydro-benzoimidazol-1-yl)-piperidin-1-yl]-acetamide | EP-628555-A1 |
| 333 | 5-Chloro-2-{2-[4-(2-oxo-2,3-dihydro-benzoimidazol-1-yl)-piperidin-1-yl]-acetyl-amino}-benzoic acid methyl ester | EP-628555-A1 |
| 334 | 5-Amino-2-{2-[4-(2-oxo-2,3-dihydro-benzoimidazol-1-yl)-piperidin-1-yl]-acetyl-amino}-benzamide | EP-628555-A1 |
| 335 | N-(2-Amino-4-benzenesulfonyl-phenyl)-2-[4-(2-oxo-2,3-dihydro-benzoimidazol-1-yl)-piperidin-1-yl]-acetamide | EP-628555-A1 |
| 336 | N-(4-Diethylamino-phenyl)-2-[4-(2-oxo-2,3-dihydro-benzoimidazol-1-yl)-piperidin-1-yl]-acetamide | EP-628555-A1 |
| 337 | 2-[4-(2-Oxo-2,3-dihydro-benzoimidazol-1-yl)-piperidin-1-yl]-N-(4-phenylamino-phenyl)-acetamide | EP-628555-A1 |
| 338 | N-(3-Dimethylamino-phenyl)-2-[4-(2-oxo-2,3-dihydro-benzoimidazol-1-yl)-piperidin-1-yl]-acetamide | EP-628555-A1 |
| 339 | N-(2-Amino-4-propylsulfanyl-phenyl)-2-[4-(2-oxo-2,3-dihydro-benzoimidazol-1-yl)-piperidin-1-yl]-acetamide; compound with GENERIC INORGANIC NEUTRAL COMPONENT | EP-628555-A1 |
| 340 | N-(7-Hydroxy-naphthalen-1-yl)-2-[4-(2-oxo-2,3-dihydro-benzoimidazol-1-yl)-piperidin-1-yl]-acetamide | EP-628555-A1 |
| 341 | N-(4-Chloro-3-nitro-phenyl)-2-[4-(2-oxo-2,3-dihydro-benzoimidazol-1-yl)-piperidin-1-yl]-acetamide | EP-628555-A1 |
| 342 | N-(4-Bromo-3-chloro-phenyl)-2-[4-(2-oxo-2,3-dihydro-benzoimidazol-1-yl)-piperidin-1-yl]-acetamide | EP-628555-A1 |
| 343 | N-(7-Butoxy-naphthalen-2-yl)-2-[4-(2-oxo-2,3-dihydro-benzoimidazol-1-yl)-piperidin-1-yl]-acetamide | EP-628555-A1 |
| 344 | N-(1H-Indazol-6-yl)-2-[4-(2-oxo-2,3-dihydro-benzoimidazol-1-yl)-piperidin-1-yl]-acetamide | EP-628555-A1 |
| 345 | N-(4-Hydroxy-phenyl)-2-[4-(2-oxo-2,3-dihydro-benzoimidazol-1-yl)-piperidin-1-yl]-acetamide | EP-628555-A1 |
| 346 | N-(4-Ethoxy-naphthalen-1-yl)-2-[4-(2-oxo-2,3-dihydro-benzoimidazol-1-yl)-piperidin-1-yl]-acetamide | EP-628555-A1 |
| 347 | N-(4-Ethoxy-phenyl)-2-[4-(2-oxo-2,3-dihydro-benzoimidazol-1-yl)-piperidin-1-yl]-acetamide | EP-628555-A1 |
| 348 | N-(2-Chloro-phenyl)-2-[4-(2-oxo-2,3-dihydro-benzoimidazol-1-yl)-piperidin-1-yl]-acetamide | EP-628555-A1 |
| 349 | 2-[4-(2-Oxo-2,3-dihydro-benzoimidazol-1-yl)-piperidin-1-yl]-N-(4-phenylazo-phenyl)-acetamide | EP-628555-A1 |
| 350 | 4-{2-[4-(2-Oxo-2,3-dihydro-benzoimidazol-1-yl)-piperidin-1-yl]-acetylamino}-benzamide | EP-628555-A1 |
| 351 | N-(4-Acetylamino-phenyl)-2-[4-(2-oxo-2,3-dihydro-benzoimidazol-1-yl)-piperidin-1-yl]-acetamide | EP-628555-A1 |
| 352 | 2-[4-(2-Oxo-2,3-dihydro-benzoimidazol-1-yl)-piperidin-1-yl]-N-(4-phenoxy-phenyl)-acetamide | EP-628555-A1 |
| 353 | N-(4-Dimethylamino-phenyl)-2-[4-(2-oxo-2,3-dihydro-benzoimidazol-1-yl)-piperidin-1-yl]-acetamide | EP-628555-A1 |
| 354 | N-(4-Acetyl-phenyl)-2-[4-(2-oxo-2,3-dihydro-benzoimidazol-1-yl)-piperidin-1-yl]-acetamide | EP-628555-A1 |
| 355 | N-(4-Nitro-phenyl)-2-[4-(2-oxo-2,3-dihydro-benzoimidazol-1-yl)-piperidin-1-yl]-acetamide | EP-628555-A1 |
| 356 | 2-[4-(2-Oxo-2,3-dihydro-benzoimidazol-1-yl)-piperidin-1-yl]-N-(4-trifluoromethyl-phenyl)-acetamide | EP-628555-A1 |
| 357 | N-(3-Chloro-4-nitro-phenyl)-2-[4-(2-oxo-2,3-dihydro-benzoimidazol-1-yl)-piperidin-1-yl]-acetamide | EP-628555-A1 |
| 358 | N-(4-Chloro-phenyl)-2-[4-(2-oxo-2,3-dihydro-benzoimidazol-1-yl)-piperidin-1-yl]-acetamide | EP-628555-A1 |
| 359 | 2-[4-(2-Oxo-2,3-dihydro-benzoimidazol-1-yl)-piperidin-1-yl]-N-p-tolyl-acetamide | EP-628555-A1 |
| 360 | 4-{2-[4-(2-Oxo-2,3-dihydro-benzoimidazol-1-yl)-piperidin-1-yl]-acetylamino}-benzoic acid methyl ester | EP-628555-A1 |
| 361 | N-(4-Methoxy-phenyl)-2-[4-(2-oxo-2,3-dihydro-benzoimidazol-1-yl)-piperidin-1-yl]-acetamide | EP-628555-A1 |
| 362 | N-(4-Cyclohexyl-phenyl)-2-morpholin-4-yl-acetamide | G & J JS 380 |

Example 6

This example describes the preparation of a tablet that includes composition 1 as prepared in Example 2.

| Formulation of a coated tablet according to the invention: | |
|---|---|
| Compound 251 of Example 3 | 583.0 mg |
| Microcrystalline cellulose | 55.0 mg |
| Corn starch | 72.0 mg |
| Poly(1-vinyl-2-pyrrolidone) | 30.0 mg |

-continued

Formulation of a coated tablet according to the invention:

| | |
|---|---|
| Highly dispersed silica | 5.0 mg |
| Magnesium stearate | 5.0 mg |
| Total | 750.0 mg |
| The tablet coating contains: | |
| Poly(O-hydroxypropyl O-methyl)-cellulose 15 cp | 6.0 mg |
| Macrogol 4000 rec. INN | 2.0 mg |
| (polyethylene glycol DAB) | 2.0 mg |
| Titanium(IV) oxide | 10.0 mg |

While the present invention has been described by means of specific embodiments, it will be understood that modifications may be made without departing from the spirit of the invention. The scope of the invention is not to be considered as limited by the description of the invention set forth in the specification and examples.

What we claim is:

1. A method for treating mammalian disorders mediated by the NPY Y5 receptor comprising administering to the mammal a therapeutically effective amount of at least one compound having the formula:

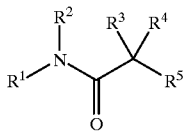

or pharmaceutically acceptable salts thereof wherein $R_1$–$R_5$ are each individually selected from the group of substituents including hydrogen, halogen, hydroxyl, thiol, lower alkyl, substituted lower alkyl, alkenyl, alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, and cyano.

2. The method according to claim 1 wherein $R^1$ is cyclohexyl; benzoyl; phenyl; phenyl substituted at least once with a lower alkyl that is in turn substituted at least once with a substituent selected from cycloalkyl, alkoxy, furan, oxo, phenyl, diisopropylamine, alkoxy, or mixtures thereof, lower alkyl, alkyl substituted at least once by oxo, phenyl, or by mixtures thereof, phenyl substituted alkene, carboxamide, carboalkoxy, methyl substituted carbophenoxy, phenyldiazo, halogen, nitro, trifluoroalkyl, amino, phenyl substituted amino, lower alkyl substituted amino, aminoacyl, sulfonylphenyl, hydroxy, alkoxy, fluoro substituted phenyl, oxazole, phenoxy, thioalkoxy, and mixtures thereof; hydroxy or alkoxy substituted naphthyl; 1H-indazole; fluorene; fluorene; and phenyl.

3. The method according to claim 1 wherein $R^2$ is selected from the group hydrogen and lower alkyl.

4. The method according to claim 1 wherein $R^3$ and $R^4$ are each individually selected from the group hydrogen, lower alkyl, and phenyl.

5. The method according to claim 1 wherein $R^3$ and $R^4$ are each individually selected from hydrogen or methyl.

6. The method according to claim 1 wherein $R^5$ is pyrrolidine; pyrrolidine substituted at least once by amino, acylamino, trifluoroacylamino, hydroxyl, carboxyl, carbobenzyloxyamino, carbomethoxyamino, carbotertbutoxyamino, alkyl substituted carbotertbutoxyamino, pyridine, lower alkyl, alkene, carboxamide, hydroxymethyl, aminoalkyl, pyrolidinemethyl, alkoxy methyl, carboxylmethyl, hydroxymethyl substituted at least once by phenyl and mixtures thereof, morpholine; piperazine substituted at least once with benzyl, phenyl, halogen substituted phenyl, and mixtures thereof, unsubstituted piperidine; substituted piperidine; piperidine substituted at least once by 2-oxo-2,3-dihydrobenzimidaz-1-ol, unsubstituted lower alkyl, lower alkyl substituted at least once by aminoethylamino, iodide, =O, piperidine, hydroxymethyl substituted piperdine, acylamino, hydroxyl, phenyl, and mixtures thereof, cyano, halogen, cyanomethylphenyl, piperidine, pyrolidine, carboxyl, phenyl, phenyl substituted at least once by trifluoromethyl, lower alkyl, halogen, and mixtures thereof, 4-oxo-1-phenyl-1,3,8-triazaspiro[4.5dec-8-yl], hydroxyl, alkoxy, carboxyl amide having the formula $CONR^8R^9$ wherein $R^8$ and $R^9$ are each individually hydrogen or lower alkyl, or $R^8$ and $R^9$ are united with a nitrogen atom to form a piperidine substituent, amino alkyl having the formula $NR^{10}R^{11}$ where $R^{10}$ and $R^{11}$ are each individually selected from lower alkyl, cycloalkyl and phenyl, a ketone having the formula —$COR^{12}$ where $R^{12}$ is phenyl substituted by halogen or alkoxy or mixtures thereof; 3,6-dihydro-2H-pyridin-1-yl; halogen substituted phenyl substituted 3,6-dihydro-2H-pyridin-1-yl; 1,3,3-trimethyl-6-aza-bicyclo[3.2.1]octyl-6-yl; 2-aza-bicyclo[2.2.1]hept-6-yl; an amine having the formula $NR^6R^7$ where $R^6$ and $R^7$ are the each individually selected from hydrogen, unsubstituted and substituted alkyl having from 1 to 10 carbon atoms, cycloalkyl, alkene, carboxy substituted alkene, lower alkyl substituted at least once by cyano, alkyne, cycloalkyl, hydroxyl, 2-hydroxyethoxy, pyridine, piperidine, pyrrolidine, piperazine, morpholine, methylpiperazine, 1-Methylpyrrol, phenyl, phenyl substituted at least once by alkoxy, halogen, carboxyl, phenoxy, hydroxy, nitro, iodine, and mixtures thereof, imidazole, 5-nitropyridylamino, furan, benzo[1,3]dioxol-5-yl, indole, alkoxy substituted indole, diethylamino, alkoxy, carboxy, trifluoromethyl, lower alkyl, hydroxymethyl, and mixtures thereof, benzyl, phenyl, benzo[1,2,5]thiadiazol, pyridine, 1,2,4-triazole, and 3-oxo-cyclohex-1-en.

7. The method according to claim 1 wherein the pharmaceutical result is the treatment of mammals with disorders selected from obesity and eating disorders.

8. The method according to claim 7 wherein the mammal is a human and the eating disorder is selected from the group consisting of bulimia and obesity.

9. The method according to claim 1 wherein the pharmaceutical result is the treatment of obesity related disorders.

10. The method according to claim 1 wherein the mammal is a human.

11. The method according to claim 1 wherein the therapeutically effective amount ranges from about 0.001 to about 100 mg/kg weight of the mammal.

12. The method according to claim 1 wherein the composition is administered orally in the form of a solution.

13. The method according to claim 1 wherein the composition is administered orally in the form of a tablet.

* * * * *